(12) United States Patent
Kim

(10) Patent No.: US 10,060,851 B2
(45) Date of Patent: Aug. 28, 2018

(54) SURFACE PLASMON DETECTION APPARATUSES AND METHODS

(71) Applicant: Plexense, Inc., Sacramento, CA (US)

(72) Inventor: Gibum Kim, Sacramento, CA (US)

(73) Assignee: PLEXENSE, INC., Yongin-Si (KR)

( * ) Notice: Subject to any disclaimer, the term of this patent is extended or adjusted under 35 U.S.C. 154(b) by 413 days.

(21) Appl. No.: 14/863,238

(22) Filed: Sep. 23, 2015

(65) Prior Publication Data

US 2016/0011109 A1  Jan. 14, 2016

Related U.S. Application Data

(63) Continuation-in-part of application No. 14/773,304, filed as application No. PCT/KR2014/001799 on
(Continued)

(30) Foreign Application Priority Data

Mar. 5, 2013 (KR) .................. 10-2013-0023326
Apr. 15, 2013 (KR) .................. 10-2013-0041228
Jul. 15, 2013 (KR) .................. 10-2013-0083142

(51) Int. Cl.
*B05D 1/18* (2006.01)
*B05D 1/00* (2006.01)
(Continued)

(52) U.S. Cl.
CPC ......... *G01N 21/554* (2013.01); *G01N 21/553* (2013.01); *H01J 37/32009* (2013.01);
(Continued)

(58) Field of Classification Search
CPC ................................ B05D 1/185; B05D 3/147
See application file for complete search history.

(56) References Cited

U.S. PATENT DOCUMENTS 6,429,023 B1    8/2002  Gharavi
6,645,343 B1 *  11/2003 Wild ................. H01J 37/32192
                                                    118/723 MW
(Continued)

FOREIGN PATENT DOCUMENTS

EP      1601512 A1   12/2005
EP      1644517 A1    4/2006
(Continued)

OTHER PUBLICATIONS

International Search Report and Written Opinion issued for International application No. PCT/US15/63954 dated Apr. 8, 2016.
(Continued)

*Primary Examiner* — Dah-Wei D. Yuan
*Assistant Examiner* — Kristen A Dagenais
(74) *Attorney, Agent, or Firm* — Knobbe, Martens, Olson & Bear LLP

(57) ABSTRACT

The disclosed technology relates to methods, apparatuses and systems for detecting molecules using surface plasmon resonance techniques, and more particularly to surface plasmon resonance techniques that employ metal nanoparticles formed on substrates. In one aspect, method of making a layer of metallic nanoparticles includes providing a liquid composition comprising a binder polymer and a solvent and at least partially immersing, into the liquid composition, an article comprising a polymeric surface, wherein the polymeric surface comprises a polymeric material and does not comprise an inorganic glass or crystalline material. The method additionally includes applying a gas phase plasma to the liquid composition to facilitate chemical reactions between the binder polymer and the polymeric material of the polymeric surface to form a binder layer on the polymeric surface of the article. The method further includes
(Continued)

applying metallic nanoparticles onto the binder layer to form a metallic nanoparticle layer on the binder layer.

18 Claims, 19 Drawing Sheets

Related U.S. Application Data

Mar. 5, 2014, and a continuation-in-part of application No. PCT/KR2013/008182, filed on Sep. 10, 2013.

(60) Provisional application No. 62/092,159, filed on Dec. 15, 2014.

(51) Int. Cl.
    G01N 21/552    (2014.01)
    H01J 37/32     (2006.01)
    B05D 3/14      (2006.01)

(52) U.S. Cl.
    CPC .... *H01J 37/3255* (2013.01); *H01J 37/32568* (2013.01); *B05D 1/185* (2013.01); *B05D 3/147* (2013.01)

(56) References Cited

U.S. PATENT DOCUMENTS

| | | | |
|---|---|---|---|
| 6,770,721 B1 * | 8/2004 | Kim | B29C 33/405 428/423.1 |
| 6,818,259 B1 * | 11/2004 | Koontz | A61L 27/28 427/536 |
| 7,327,000 B2 | 2/2008 | DeHeer et al. | |
| 7,652,760 B1 | 1/2010 | Simpson et al. | |
| 7,731,826 B2 | 6/2010 | Hibbs et al. | |
| 2002/0128234 A1 * | 9/2002 | Hubbell | A61B 5/14546 514/100 |
| 2003/0082237 A1 | 5/2003 | Cha et al. | |
| 2004/0154541 A1 | 8/2004 | Colpo et al. | |
| 2007/0154351 A1 | 7/2007 | Bae et al. | |
| 2007/0178280 A1 | 8/2007 | Bower et al. | |
| 2008/0044592 A1 | 2/2008 | Elkin et al. | |
| 2009/0142789 A1 | 6/2009 | Aastrup et al. | |
| 2009/0209420 A1 | 8/2009 | Kalgutkar et al. | |
| 2010/0134799 A1 | 6/2010 | Huh et al. | |
| 2010/0215555 A1 * | 8/2010 | Jin | B01J 35/0006 422/222 |
| 2011/0207237 A1 | 8/2011 | Sai et al. | |
| 2011/0281070 A1 | 11/2011 | Mittal et al. | |
| 2011/0297212 A1 | 12/2011 | Wu et al. | |
| 2012/0241693 A1 | 9/2012 | Magdassi et al. | |
| 2013/0029057 A1 * | 1/2013 | Laksin | B05D 3/0493 427/488 |
| 2014/0132954 A1 | 5/2014 | Kang et al. | |

FOREIGN PATENT DOCUMENTS

| | | | | |
|---|---|---|---|---|
| EP | 2128598 | A1 * | 12/2009 | ........... G01N 21/554 |
| EP | 2128598 | A1 | 12/2009 | |
| EP | 1676330 | B1 | 5/2010 | |
| EP | 2386070 | A1 | 11/2011 | |
| EP | 2391657 | A1 | 12/2011 | |
| JP | 62-102139 | A | 5/1987 | |
| JP | 62-187248 | A | 8/1987 | |
| JP | 7-47265 | A | 2/1995 | |
| JP | 10-307104 | A | 11/1998 | |
| JP | 2002-357540 | A | 12/2002 | |
| JP | 3730652 | B2 | 10/2005 | |
| JP | 3897703 | B2 | 1/2007 | |
| JP | 2008-175615 | A | 7/2008 | |
| JP | 2008-216055 | A | 9/2008 | |
| JP | 2008-232853 | A | 10/2008 | |
| JP | 4220879 | B2 | 11/2008 | |
| JP | 4481967 | B2 | 3/2010 | |
| JP | 2012-098211 | A | 5/2012 | |
| JP | 2012-132886 | A | 7/2012 | |
| KR | 10-0136144 | B1 | 1/1998 | |
| KR | 10-0265692 | B1 | 9/2000 | |
| KR | 10-2002-0075387 | A | 10/2002 | |
| KR | 10-0465278 | B1 | 1/2005 | |
| KR | 10-0480340 | B1 | 3/2005 | |
| KR | 10-2006-0094409 | A | 8/2006 | |
| KR | 10-0662021 | B1 | 12/2006 | |
| KR | 10-2007-0100325 | A | 10/2007 | |
| KR | 10-0787046 | B1 | 12/2007 | |
| KR | 10-0860958 | B1 | 9/2008 | |
| KR | 10-2009-0060635 | A | 6/2009 | |
| KR | 10-0928546 | B1 | 11/2009 | |
| KR | 10-2010-0014314 | A | 2/2010 | |
| KR | 10-2010-0061603 | A | 6/2010 | |
| KR | 10-2010-0063316 | A | 6/2010 | |
| KR | 10-0962290 | B1 | 6/2010 | |
| KR | 10-2010-0106263 | A | 10/2010 | |
| KR | 10-0987993 | B1 | 10/2010 | |
| KR | 10-0991011 | B1 | 10/2010 | |
| KR | 10-0996450 | B1 | 11/2010 | |
| KR | 10-1017994 | B1 | 3/2011 | |
| KR | 10-1027795 | B1 | 4/2011 | |
| KR | 10-1029115 | B1 | 4/2011 | |
| KR | 10-2011-0124489 | A | 11/2011 | |
| KR | 10-1079271 | B1 | 11/2011 | |
| KR | 10-1081336 | B1 | 11/2011 | |
| KR | 10-1097882 | B1 | 12/2011 | |
| KR | 10-2012-0013770 | A | 2/2012 | |
| KR | 10-2012-0014206 | A | 2/2012 | |
| KR | 10-2012-0016598 | A | 2/2012 | |
| KR | 10-1124618 | B1 | 3/2012 | |
| KR | 10-1134349 | B1 | 4/2012 | |
| KR | 10-1145133 | B1 | 5/2012 | |
| KR | 10-1145660 | B1 | 5/2012 | |
| KR | 10-2012-0084529 | A | 7/2012 | |
| KR | 10-1175977 | B1 | 8/2012 | |
| KR | 10-2012-0136912 | A | 12/2012 | |
| KR | 10-2013-0000583 | A | 1/2013 | |
| KR | 10-2013-0006169 | A | 1/2013 | |
| KR | 10-2013-0015806 | A | 2/2013 | |
| KR | 10-1238551 | B1 | 3/2013 | |
| KR | 10-1239356 | B1 | 3/2013 | |
| KR | 10-1254666 | B1 | 4/2013 | |
| KR | 10-1271418 | B1 | 6/2013 | |
| KR | 10-1328190 | B1 | 11/2013 | |
| KR | 10-1335032 | B1 | 12/2013 | |
| KR | 10-2014-0124316 | A | 10/2014 | |
| WO | 2004-080681 | A1 | 9/2004 | |
| WO | 2005-001120 | A1 | 6/2005 | |
| WO | 2010-078666 | A1 | 7/2010 | |
| WO | 2010-085945 | A1 | 8/2010 | |
| WO | 2012-111991 | A9 | 8/2012 | |
| WO | 2012-157403 | A1 | 11/2012 | |
| WO | 2014-137152 | A1 | 9/2014 | |
| WO | 2014-171597 | A1 | 10/2014 | |

OTHER PUBLICATIONS

C.-P. Klages, et al, "Microplasma-Based Treatment of Inner Surfaces in Microfluidic Devices", Contrib. Plasma Phys. 47, No. 1-2, pp. 49-56 (2007).

Osamu Takai, "Solution plasma processing (SPP)", Pure Appl. Chem., vol. 80, No. 9, pp. 2003-2011, 2008—9 pages.

Sung Min Kim, et al., "Effects of PVP and KCl concentrations on the synthesis of gold nanoparticles using a solution plasma processing", Department of Material Engineering, Korea Aerospace University and Research Institute for Aerospace Engineering—3 pages.

Khoren Sahagian, et al, "Why and How to Use Gas Plasma Technology for Surface Treatment in Medical Devices", Published on MDDI Medical Device and Diagnostic Industry News Products and Suppliers (http://www.mddionline.com)—7 pages.

Christiane Gottschalk et al., "Using dissolved ozone in semiconductor cleaning applications", Micro, A Canon Communications LLC Publication, Mar. 2004—6 pages.

(56) References Cited

OTHER PUBLICATIONS

Anjum Qureshi, et al, "Surface Modification of Polycarbonate by Plasma Treatment", iopscience.iop.org, Journal of Physics: Conference Series 208 (2010) 012108—7 pages.

Peter Bruggeman, et al., "Non-thermal plasmas in and in contact with liquids", J. Phys. D: Appl. Phys. 42 (2009) 053001—29 pages.

Helena Oi Lun Li, et al., "Comparison between the Mechanism of Liquid Plasma Discharge Process in Water and Organic Solution", Green Mobility Collaborative Research Center, Nagoya University, Graduate School of Engineering, Nagoya University, dated Dec. 14, 2012, pp. 22-27.

K. Baba, et al., "Ion irradiation effects on ionic liquids interfaced with rf discharge plasmas", Department of Electronic Engineering, Tohoku University, Sendai 980-8579, Japan, Appl. Phys. Lett. 90, 201501 2007—4 pages.

Rajesh Dorai, et al., "Plasma Surface Modification of Polymers Using Atmospheric Pressure Discharges", University of Illinois Department of Chemical Engineering and Department of Electrical and Computer Engineering—32 pages.

Dorota Kregiel, et al., "Effect of Plasma Processing and Organosilane Modifications of Polyethylene on Aeromonas hydrophila Biofilm Formation", Hindawi Publishing Corporation BioMed Research International vol. 2014, Article ID 232514—9 pages.

Ron Nickerson, "Plasma Surface Modification for Cleaning and Adhesion", AST Products, Inc.—6 pages.

Nina Recek, et al., "Protein Adsorption on Various Plasma-Treated Polyethylene Terephthalate Substrates", Molecules 2013, 18, 12441-12463; doi:10.3390/molecules181012441—23 pages.

Qiang Chen, et al., "Plasma-Liquid Interaction: a New Way to Synthesize Nanomaterials", Fujian Provincial Key Laboratory of Plasma and Magnetic Resonance, School of Physics and Mechanical and Electrical Engineering, Department of Physics, Lanzhou University and State Key Laboratory of Heavy Oil Processing, China University of Petroleum—73 pages.

Plasma Surface Modification of Polymers, 2007 PLASMATech—2 pages.

Toshiro Kaneko, et al., "Plasma Process on Ionic Liquid Substrate for Morphology Controlled Nanoparticles", http://dx.doi.org/10.5772/52095—16 pages.

Dr. James D. Getty, March Plasma Systems, "How Plasma-Enhanced Surface Modification Improves the Production of Microelectronics and Optoelectronics", Chip Scale Review 2002—pp. 72-75.

Frank Endres, et al., "Electrodeposition from Ionic Liquids", Yokohama, Japan, Dec. 2007—399 pages.

Yudai Minagawa, et al., "Analysis of effect of ion irradiation to liquid surface on water molecule kinetics by classical molecular dynamics simulation", iopscience.iop.org—8 pages.

Kenichi Uemura, et al., "Cleaning Technology of Silicon Wafers", Nippon Steel Technical Report No. 83 Jan. 2001—8 pages.

V. Colombo, et al., "Atmospheric Plasma Surface Modification of Electrospun Poly(L-Lactic Acid): Effect on Mat Properties and Cell Culturing", 22nd Annual BioInterface Conference, Oct. 2012—32 pages.

International Search Report dated Jun. 3, 2014 of related PCT Application No. PCT/KR2014/001799 and its English translation—4 pages.

International Search Report dated Jan. 9, 2014 of related PCT Application No. PCT/KR2013/008182 and its English translation—4 pages.

Invitation to Pay Additional Fees issued by the International Searching Authority in International Application No. PCT/US15/63954 dated Feb. 10, 2016.

\* cited by examiner

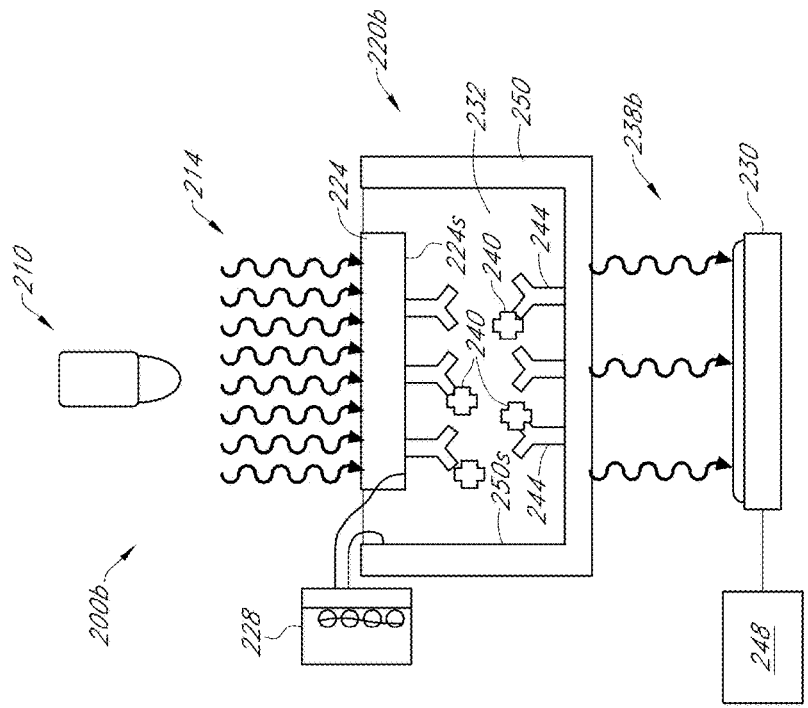
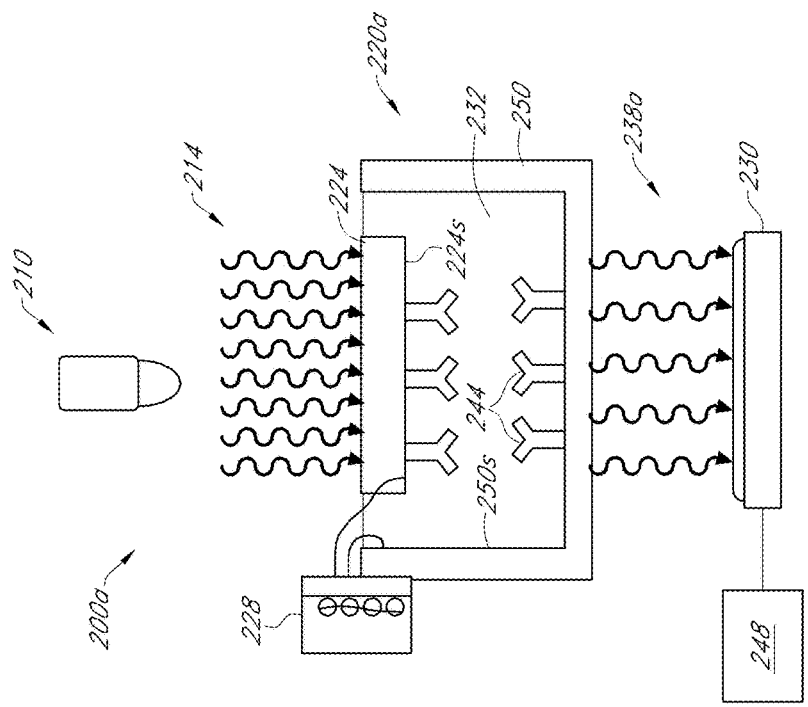

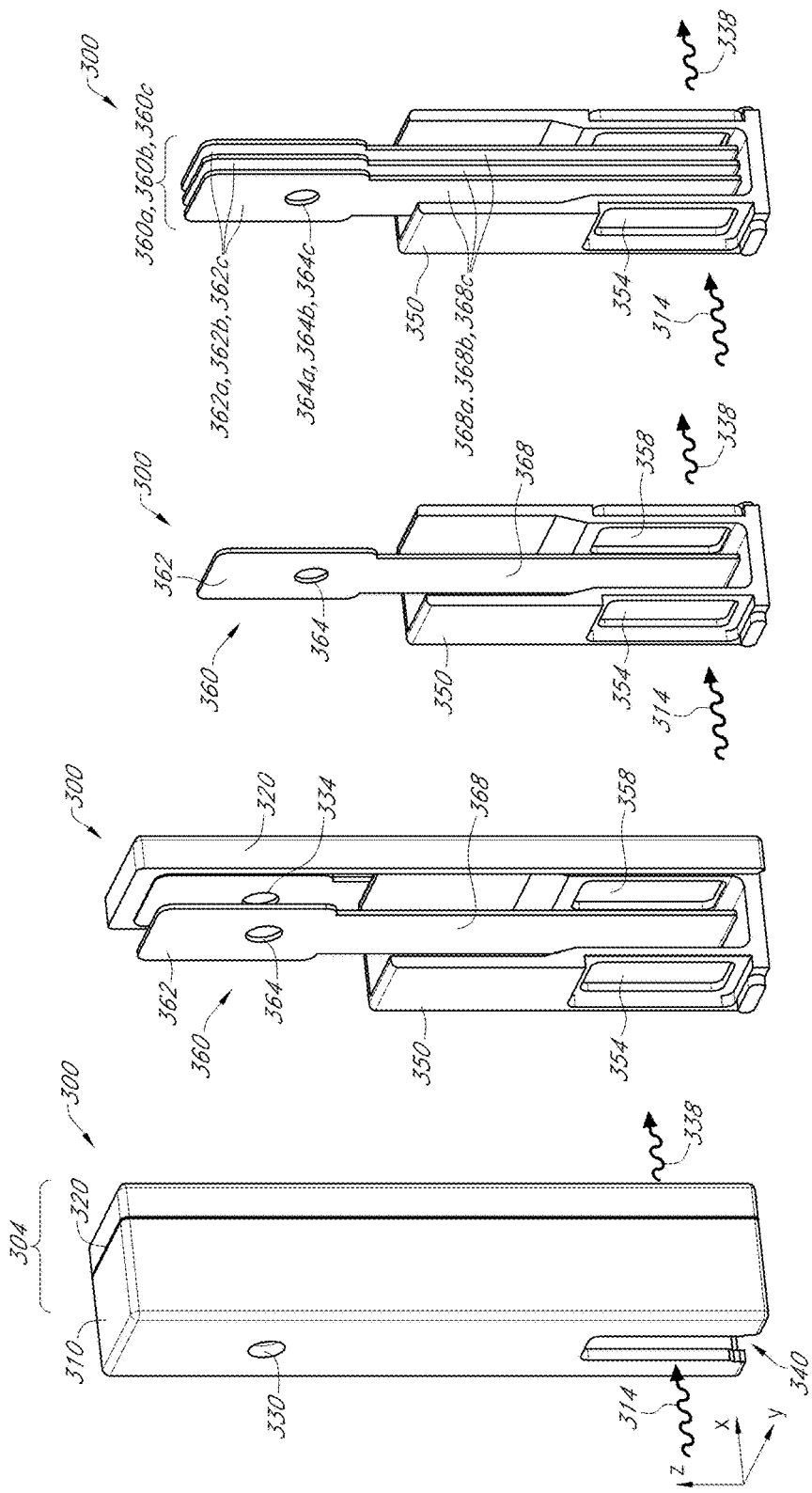

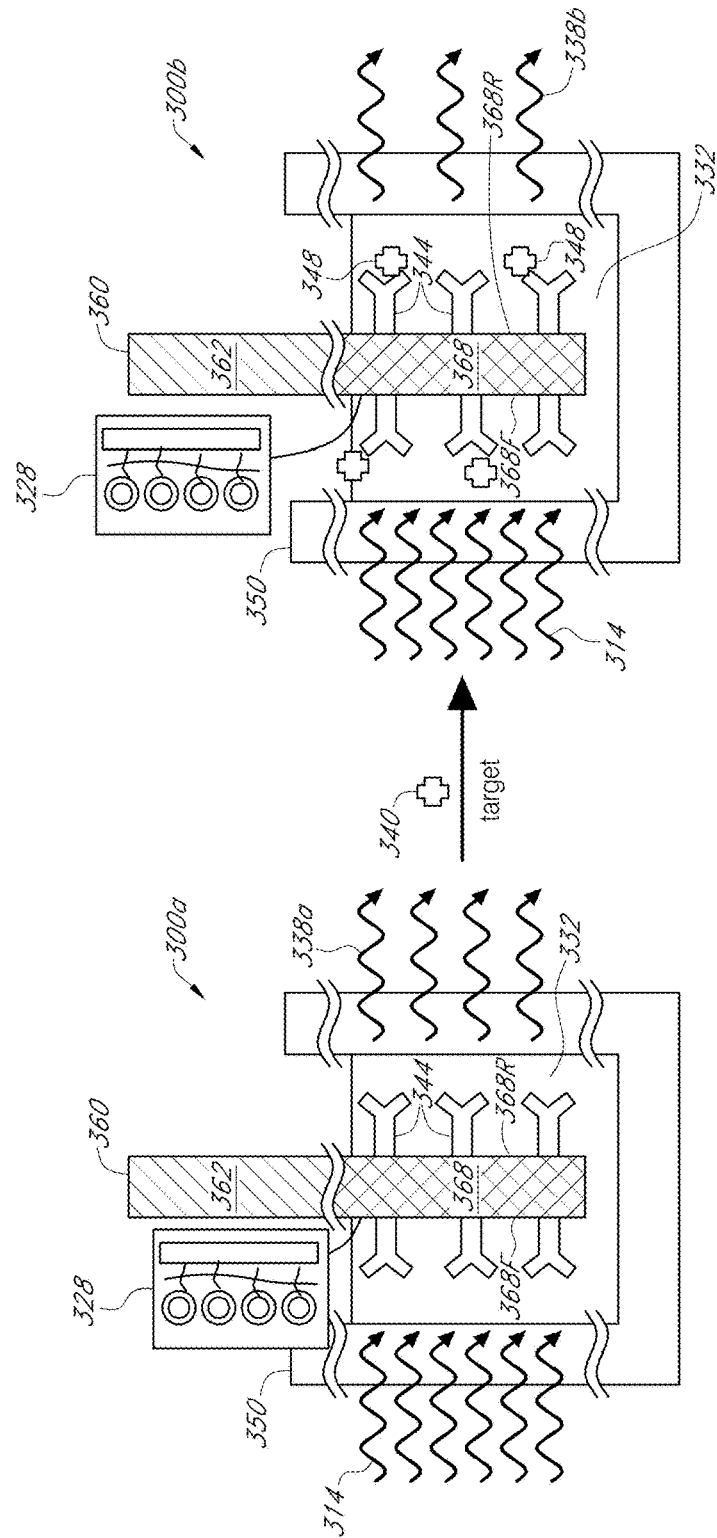

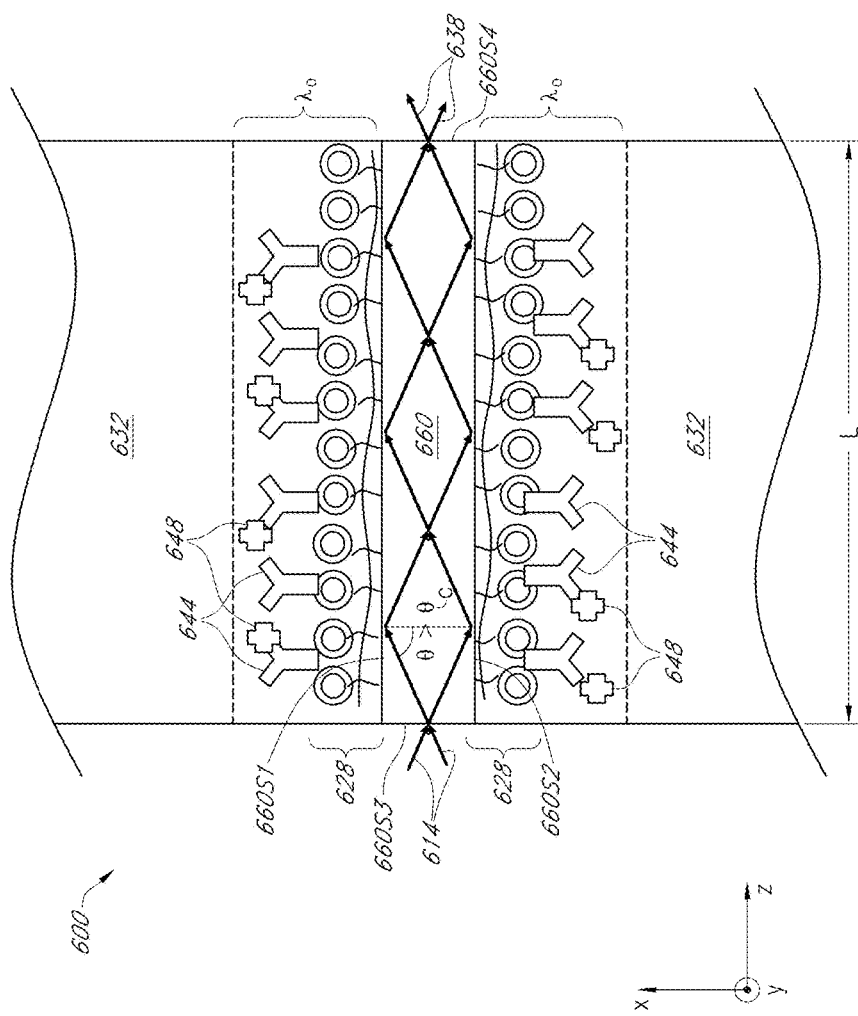

SURFACE PLASMON DETECTION APPARATUSES AND METHODS

CROSS-REFERENCE TO RELATED APPLICATION

Any and all applications for which a foreign or domestic priority claim is identified in the Application Data Sheet as filed with the present application are hereby incorporated by reference under 37 CFR 1.57.

BACKGROUND

Field

The disclosed technology relates to methods, apparatuses and systems for detecting molecules using surface plasmon resonance techniques, and more particularly to surface plasmon resonance techniques that employ metal particles formed on substrates.

Description of the Related Art

A surface plasmon (SP) refers to coherent electron oscillation that propagates along an interface between a dielectric (e.g. silica glass) and a metal (e.g. Ag or Au) together with an electromagnetic wave, e.g., light. Under certain conditions (defined by of wavelength, polarization and/or incidence angle), free electrons at the surface of the metal absorb incident light photons and convert them into surface plasmon waves. A resonance condition, referred to as surface plasmon resonance (SPR), can be established when the frequency of light photons matches the natural frequency of surface electrons oscillating against the restoring force of positive nuclei of the metal. The SPR condition can be used to for in optical measurements such as fluorescence, Raman scattering, second harmonic generation, and absorption, among others.

SUMMARY

In one aspect, a method of forming a layer of metallic nanoparticles includes providing a liquid composition comprising a binder polymer and a solvent and at least partially immersing, into the liquid composition, an article comprising a polymeric surface, wherein the polymeric surface comprises a polymeric material and does not comprise an inorganic glass or crystalline material. The method additionally includes applying a gas phase plasma to the liquid composition to facilitate chemical reactions between the binder polymer and the polymeric material of the polymeric surface to form a binder layer on the polymeric surface of the article. The method further includes applying metallic nanoparticles onto the binder layer to form a metallic nanoparticle layer on the binder layer.

In some embodiments, the binder polymer comprises a plurality of amine terminals, wherein at least part of the amine terminals participate in the chemical reaction with the polymeric material to form allylamine bonds.

In some embodiments the binder polymer comprises one or more molecules capable of forming an amide bonding, the binder polymer selected from the group consisting of linear or multi-branched a cationic polymer such as poly diallyl dimethyl ammonium, poly diallydimethylammonium chloride, poly allylamine hydrochloride, poly 4-vinylbenzyltrimethyl ammonium chloride, polyamines derived from ethylenamine including diethylenetriamine (DETA), ($H_2N$—$CH_2CH_2$—NH—$CH_2CH_2$—$NH_2$, an analog of diethylene glycol), triethylenetetramine (TETA), ($H_2N$—$CH_2CH_2$—NH—$CH_2CH_2$—NH—$CH_2CH_2$—$NH_2$), tetraethylenepentamine (TEPA), ($H_2N$—$CH_2CH_2$—NH—$CH_2CH_2$—NH—$CH_2CH_2$—NH—$CH_2CH_2$—$NH_2$), pentaethylenehexamine (PEHA) ($H_2N$—$CH_2CH_2$—NH—$CH_2CH_2$—NH—$CH_2CH_2$—NH—$CH_2CH_2$—NH—$CH_2CH_2$—$NH_2$), polyethylene amine, hyperbranched polymers including polyamidoamine dendrimers, polypropylimine dendrimers, polyethyleneimine (PEI), or a mixture thereof. In other embodiments, the binder polymer 804 includes an anionic polymer such as poly acrylic acid, poly sodium 4-styrene sulfonate, poly vinylsulfonic acid, poly sodium salt, poly amino acids, or a mixture thereof. In some embodiments, binder polymers include linear or multi-branched polyethyleneimine (PEI), ethylenediamine or other crosslinkable molecules suitable for forming amide bonds on a surface of a polymeric substrate. In some embodiments, the polymeric surface does not include non-polymeric materials.

In some embodiments, the polymeric material does not include $SiO_2$ or $Al_2O_3$.

In some embodiments, the polymeric surface comprises an optically transparent polymeric material selected from the group consisting of polyethylene terephthalate (PET, polyethyleneterephthalate), polymethyl methacrylate (PMMA, polymethylmethacylate), polystyrene (PS, polystyrene), polycarbonate (PC, polycarbonate) and combinations thereof.

In some embodiments, providing the liquid composition includes providing the liquid composition in an electrically insulating dielectric container, wherein the container is placed between two electrodes of a plasma chamber when applying the gas phase plasma.

In some embodiments, applying the gas phase plasma includes applying the gas phase plasma such that the liquid composition and the article immersed therein are electrically floating.

In some embodiments, the article is immersed into the liquid composition such that an entire polymeric surface is submerged under the liquid composition when applying the plasma to the liquid composition.

In some embodiments, applying the gas phase plasma includes applying the gas phase plasma that is formed from a gas mixture which includes a substantial amount of oxygen gas.

In some embodiments, applying the gas phase plasma includes applying the gas phase plasma that is formed from a gas mixture which does not include a substantial amount of ammonia gas.

In some embodiments, the method of forming the layer of metallic nanoparticles further comprises, after forming the binder layer, extinguishing the gas phase plasma prior to applying the metallic nanoparticles.

In some embodiments, wherein the article has in a shape selected from the group consisting of a sheet, a strip, a cavity, a column, a cylinder, a fiber, a coil, a U-shape, a helix and a spiral.

In some embodiments, forming the metallic nanoparticle layer comprises forming the metallic nanoparticles on a polymeric surface of the article which faces away from the gas phase plasma.

In some embodiments, the metallic nanoparticles comprise negatively charged metallic balls, wherein the metallic nanoparticles are bound with free amine terminals of the binder layer.

In some embodiments, the metallic nanoparticles comprise gold nanoparticles.

In some embodiments, at least part of the metallic nanoparticles comprises metallic balls, wherein one or more ligands are attached to metallic balls.

In some embodiments, the one or more ligands comprise a link and a chemical moiety having specificity to one or more target molecules.

In some embodiments, the metallic nanoparticle layer has an area particle density between about $1.0 \times 10^9$ nanoparticles/cm$^2$ and about $2.0 \times 10^{11}$ nanoparticles/cm$^2$.

In some embodiments, the metallic nanoparticles have a median size between about 1 nm and about 10 nm, between about 5 nm and about 20 nm, between about 10 nm and about 30 nm, between about 20 nm and about 40 nm, between about 30 nm and about 50 nm, between about 40 nm and about 60 nm, between about 50 nm and about 80 nm, between about 60 nm and about 100 nm, between about 80 nm and about 150 nm, between about 100 nm and about 200 nm, between about 150 nm and about 250 nm, between about 200 nm and about 300 nm, between about 250 nm and about 400 nm, between about 300 nm and about 700 nm, or between about 500 nm and about 900 nm, or between about 700 nm and about 1100 nm.

In some embodiments, the article comprises a polymeric fiber, wherein the polymeric fiber comprises at least one selected from the group consisting of a straight portion, a curved portion and a coiled portion.

In another aspect, a test vehicle for detecting a target contained in a liquid sample has a body comprising a polymeric surface, wherein the polymeric surface includes a first polymeric material and does not comprise an inorganic glass or crystalline material. The test vehicle additionally includes a metallic nanoparticle layer formed over the polymeric surface. The test vehicle further includes one or more ligands attached to the metallic nanoparticle layer and having specificity to one or more target molecule.

In some embodiments, the test vehicle further comprises a binder polymer layer interposed between the polymeric surface and the metallic nanoparticle layer, wherein the binder layer comprises a second polymeric material that is different from the first polymeric material.

In some embodiments, the body includes portion having a shape selected from the group consisting of a sheet, a strip, a cavity, a column, a cylinder, a fiber, a coil, a U-shape, a helix and a spiral.

In some embodiments, the first polymeric material comprises one or more selected from the group consisting of polycarbonate (PC), polyethylene terephthalate, polymethyl methacrylate, triacetyl cellulose (TAC), cyclic olefins, polyethylene terephthalate, polyarylate, polyethylene terephthalate, polybutylene terephthalate, polyimide and combinations thereof.

In some embodiments, the body comprises at least one surface that is covered by a metallic nanoparticle layer.

In some embodiments, the body comprises at least one surface that is not covered by a metallic nanoparticle layer.

In some embodiments, the test vehicle includes a cuvette configured to contain the liquid sample.

In some embodiments, the metallic nanoparticle layer is formed over the one or more inner surfaces of the cuvette.

In some embodiments, the body is in the form of a fiber having a first end for receiving light beams therethrough and a second end for emitting light beams therethrough.

In some embodiments, between the first and second ends the fiber comprises at least one selected from the group consisting of a straight portion and a curved portion.

In some embodiments, the body comprises a coiled structure.

In some embodiments, the body comprises a U-shaped structure.

In some embodiments, the body comprises a column structure having a first end for receiving light beams therethrough and a second end for emitting light beams therethrough.

In some embodiments, the metallic nanoparticle layer comprises negatively charged metallic balls, wherein the metallic nanoparticles are bound with free amine terminals of the binder layer.

In some embodiments, the metallic nanoparticle layer comprises gold nanoparticles.

In some embodiments, at least part of the metallic nanoparticles comprises metallic balls, wherein the one or more ligands are attached to metallic balls.

In some embodiments, the one or more ligands comprise a link and a chemical moiety having specificity to one or more targets.

In some embodiments, the metallic nanoparticle layer has an area particle density between about $1 \times 10^9$ nanoparticles/cm$^2$ and about $2 \times 10^{11}$ nanoparticles/cm$^2$.

In some embodiments, the metallic nanoparticle layer has nanoparticles having a median size between about 1 nm and about 10 nm, between about 5 nm and about 20 nm, between about 10 nm and about 30 nm, between about 20 nm and about 40 nm, between about 30 nm and about 50 nm, between about 40 nm and about 60 nm, between about 50 nm and about 80 nm, between about 60 nm and about 100 nm, between about 80 nm and about 150 nm, between about 100 nm and about 200 nm, between about 150 nm and about 250 nm, between about 200 nm and about 300 nm, between about 250 nm and about 400 nm, between about 300 nm and about 700 nm, or between about 500 nm and about 900 nm or between about 700 nm about 1100 nm.

In another aspect, a method of detecting target molecules includes providing a test vehicle comprising a transparent container configured to receive therein at least one substrate comprising a polymeric surface and to receive a liquid solution comprising the target molecules. The polymeric surface has formed thereon a binder polymer layer and a plurality of metallic nanoparticles. The test vehicle further includes capturing molecules attached to at least some of the metallic nanoparticles, the capturing molecules adapted to capture one or more of the target molecules. The method additionally includes receiving the liquid solution in the transparent container and submerging at least a portion of the polymeric surface in the liquid solution, thereby capturing at least some of the target molecules with the capturing molecules. The method further includes transmitting light through at least one of a first surface of the substrate and a second surface of the substrate, and detecting transmitted light that has been modified from an incident light by localized surface plasmon resonance (LSPR) of the metallic nanoparticle caused by the light being transmitted.

In some embodiments, chains of the binder polymer are bound to the polymeric surface by a plurality of amide bonds formed therebetween.

In some embodiments the at least one of the first surface and the second surface includes the polymeric surface, and transmitting includes transmitting the light through the polymeric surface before detecting.

In some embodiments, each of the first surface and the second surface includes a respective first polymeric surface and a second polymeric surface, and transmitting includes transmitting through the first and second polymeric surfaces before detecting.

In some embodiments, providing the test vehicle includes providing a plurality of substrates each having a polymeric surface, and wherein transmitting includes transmitting the light through each of the polymeric surfaces of the plurality of substrates.

In some embodiments, the at least one of the first surface and the second surface does not include the polymeric surface, and the light being detected is not transmitted through the polymeric surface before being detected.

In some embodiments, the substrate has a first refractive index that is higher than a second refractive index of the liquid solution, and transmitting includes receiving the light through the first surface and transmitting under a total internal reflection (TIR) or attenuated total internal reflection (ATR) condition such that the light is reflected from the polymeric surface a plurality of times before being transmitted through the second surface.

In some embodiments, providing the test vehicle includes providing the polymeric surface has at least one of a curvature, a flection, an arc, a bend, a bow, a twist, a loop and a turn.

In some embodiments, providing the test vehicle includes providing between the first and second surfaces of the substrate at least one selected from the group consisting of a straight portion and a curved portion.

In some embodiments, providing the test vehicle includes providing a coiled structure between the first and second surfaces.

In some embodiments, providing the test vehicle includes providing a U-shaped structure between the first and second surfaces.

In some embodiments, providing the test vehicle includes providing a column structure between the first and second surfaces.

In another aspect, a method of forming a polymer layer on a polymeric surface includes providing in a container a liquid composition comprising a binder polymer and a solvent. The binder polymer has a plurality of binder functional groups. The method additionally includes at least partially submerging an article in the liquid composition, wherein a submerged portion of the article comprises a polymeric surface having formed thereon a plurality of substrate functional groups. The method additionally includes disposing the container having at least partially submerged therein the article in a plasma chamber. The method further includes applying energy to a volume of gas above a surface of the liquid to generate a plasma from the volume of gas, thereby causing or accelerating formation of a binder polymer layer on the polymeric surface.

In some embodiments, a chemical reaction between some of the polymer functional groups and some of the substrate functional groups causes the formation of the binder polymer layer.

In some embodiments, applying the energy includes providing power to at least one electrode that does not contact the liquid composition.

In some embodiments, causing or accelerating the formation of the polymer layer includes forming the polymer layer on the polymeric surface that is submerged such that the liquid composition is interposed between the polymeric surface and the plasma, and such that the polymeric surface does not come in direct contact with the plasma.

In some embodiments, the polymeric surface on which the polymer layer is formed faces away from the plasma.

In some embodiments, causing or accelerating the formation of the polymer layer includes forming the binder polymer layer on the polymeric surface which has at least one of a curvature, a flection, an arc, a bend, a bow, a twist, a loop and a turn.

In some embodiments, causing or accelerating formation of the binder polymer layer includes forming a polymer layer that has a substantially uniform thickness on the polymeric surface having the at least one of the curvature, a flection, an arc, a bend, a bow, a twist, a loop and a turn.

In some embodiments, causing or accelerating the formation of the binder polymer layer includes forming the binder polymer layer on the polymeric surface which faces away from the plasma.

In some embodiments, the polymer functional groups include $NH_2$ group.

In some embodiments, the substrate functional groups include carbonate group (—O—(C=O)—O—).

In some embodiments, a chemical reaction between some of the binder functional groups and some of the substrate functional groups causes formation of amide bonds therebetween.

In some embodiments, the volume of gas does not contain nitrogen, and the nitrogen atoms of the $NH_2$ groups forms the amide bond.

In some embodiments, the container is an electrically insulating container.

In some embodiments, the liquid composition comprises water.

In some embodiments, the liquid further comprise NaOH dissolved therein.

In some embodiments, the binder polymer comprises polyethyleneimine (PEI) or PEI with a portion of terminal amines (—$NH_2$) that are replaced with sulfur hydride (—SH).

In some embodiments, the method of forming the polymer layer further comprises, after causing or accelerating the chemical reaction, attaching nanoparticles to the binder polymer chains.

In some embodiments, the nanoparticles are attached to some of remaining binder functional groups of the binder polymer different from the binder functional groups attached to some of the substrate functional groups.

In some embodiments, the container is an insulating substrate such that the polymeric substrate and the liquid composition is electrically floating when the energy is applied to form the plasma.

In some embodiments, the energy is pulsed DC energy.

In some embodiments, the plasma is generated from the volume of gas at atmospheric pressure.

In some embodiments, the energy is delivered through a first electrode, wherein the container is disposed on another electrode that does not contact the liquid composition or the polymeric substrate.

BRIEF DESCRIPTION OF THE DRAWINGS

FIG. 2A is a schematic illustration of a localized plasmon resonance (LSPR) measurement system according to embodiments.

FIG. 2B is a schematic illustration of the localized plasmon resonance (LSPR) measurement system of FIG. 2A after exposure to target molecules, according to embodiments.

FIG. 3A is a polymer-based LSPR test vehicle illustrated with a case, according to an embodiment.

FIG. 3B is the polymer-based LSPR test of FIG. 3A illustrated without a front portion of the case, showing a cross-sectional view of a container and a substrate disposed therein, according to an embodiment.

FIG. 3C is the polymer-based LSPR test vehicle of FIG. 3A illustrated without the case, showing a cross-sectional view of a container and a substrate disposed therein, according to an embodiment.

FIG. 3D is the polymer-based LSPR test vehicle of FIG. 3A illustrated without the case, showing a cross-sectional view of a container and a plurality of substrates disposed therein, according to an embodiment.

FIG. 3E is a schematic illustration of a polymer-based LSPR test vehicle having a substrate coated with nanoparticles and capturing molecules, according to embodiments.

FIG. 3F is a schematic illustration of a polymer-based LSPR test vehicle of FIG. 3E having target molecules captured by at least a subset of the capturing molecules, according to embodiments.

FIG. 6A is a schematic illustration of a polymer-based attenuated total reflection (ATR) LSPR test vehicle under an ATR mode of operation, according to embodiments.

DETAILED DESCRIPTION OF ILLUSTRATIVE EMBODIMENTS

Surface Plasmon Resonance (SPR) Measurement Apparatuses and Systems

The surface plasma resonance (SPR) condition can be used to detect the presence of certain target molecules, e.g., polymers, DNA or proteins, etc., that may be chemically bound, adsorbed or otherwise attached on a metal (e.g., gold and silver) surface, by measuring the angle of reflection minimum (or absorption maximum) of light. For example, the presence of the target molecules can be detected by utilizing certain capturing molecules that are configured to capture the target molecules or interact, bond or bind with the target molecules. When the capturing molecules, which may be immobilized on the surface of the metal, capture the target molecules, perturbations at the metal surface may be caused, which can in turn induce a modification of the SPR condition. Such a modification can be measured as a change in reflectivity of a test vehicle, and forms the basis for some SPR-based measurement techniques that are adapted for measuring the presence of a wide variety of target molecules.

Planar SPR Measurement System

Figure 1:
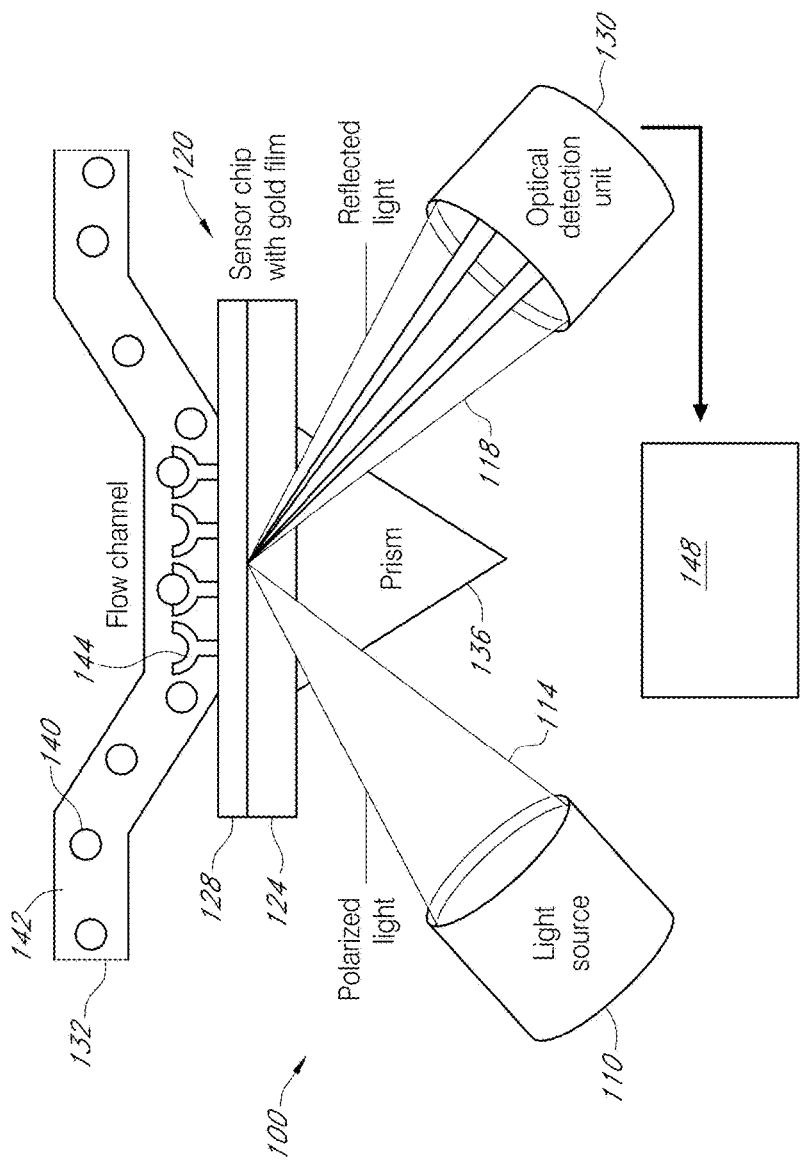
FIG. 1 is a schematic illustration of a surface plasmon resonance (SPR) measurement system.

FIG. 1 illustrates a planar metal thin film-based SPR measurement system 100 according to one embodiment for detecting the presence of target molecules using a test vehicle 120. The planar SPR measurement system 100 includes a light source 110 for illuminating a test vehicle 120 with incident light 114, e.g., polarized incident light, and a detector 130, e.g., a photodetector, for receiving a reflected light 118 at a range of wavelengths. The test vehicle 120 includes a substrate 124, a thin metal film 128 formed on one side of the substrate 124, and a glass block 136, or a suitable monochromator, disposed on the other side of the substrate 124. The test vehicle 120 additionally includes a channel 132 for delivering a solution 142 to the surface of the thin metal film 128. The solution 142 includes an analyte that may contain target molecules 140 to be detected by the measurement system 100. The surface of the metal film 128 has attached thereto capturing molecules 144, sometimes called ligands, that are configured to capture (interact, bond or bind with) the target molecules 140 that may be present in the solution. Thus, by contacting the surface of the metal film 128 to the solution 142, at least some capturing molecules 144 can capture and bind target molecules 140 thereto, which can modify a resonance condition of the surface plasmons of the metal film 128.

In operation, the light source 110 illuminates one side of the glass block 136 with an incident light 114. In some configurations, the thin metal film 128 (e.g., gold), is positioned sufficiently close to the glass block 136, e.g., is in contact therewith, such that an evanescent wave of the incident light 114 can interact with the plasma waves on the surface of the metal film 128, thereby excite the plasmons of the metal film 128. In the planar SPR measurement system 100 of FIG. 1, perturbations at the metal surface 128 that induce a modification of the resonance condition of the plasmons of the metal film 128 can be caused when the target molecules 140 are bound to or captured by at least some of the capturing molecules 144. The perturbations can in turn induce a change in reflectivity that can be measured by the detector 130, whose signal can subsequently be analyzed by an analysis unit 148. In the illustrated system 100, some target molecules 140 can chemically bind to the capturing molecules when the solution 142 is injected through the channel 132, thereby causing an increase in the refractive index that is proportional to the bound concentration of the target molecules 140. In this way, the illustrated SPR measurement system 100 allows for measurement of the interaction between the capturing molecules 144 and the target molecules 140.

Metal thin film-based SPR measurement techniques remain difficult and/or expensive to implement for several reasons. One reason is related to the fact that many existing techniques for forming thin metal films can limit the shapes and surfaces of substrates onto which the metal films are formed. For example, thermal chemical vapor deposition often requires temperatures that are unsuitable for substrates such as polymeric substrates. In other deposition techniques such as physical vapor deposition or plasma enhanced chemical vapor deposition, shadowing effects may result in uneven thicknesses. In some techniques that may be conformal such as plating, special seeding layers may be needed. In yet other conformal techniques such as atomic layer deposition, the rate of deposition may be slow. Furthermore, relatively high cost may be associated with fabricating test vehicles having complex shapes for enhanced sensitivity and/or versatility. Another reason that many metal film-based SPR techniques remain difficult to implement relates to obtaining accurate and reliable quantitative signals in changing environmental factors such as temperature. Thus, in the following, various embodiments disclosed relate to test vehicles, systems, and methods with improved sensitivity, versatility and reliability of SPR-based measurement techniques using nanoparticle-based localized SPR (LSPR).

Localized Surface Plasmon (LSPR) Measurement System

FIGS. 2A and 2B illustrate a localized surface plasmon resonance (LSPR) measurement system 200a/b for detecting target molecules that may be attached to a surface of a test vehicle, according to embodiments. FIG. 2A illustrates the LSPR measurement system 200a prior to introducing the target molecules to be detected, and FIG. 2B illustrates the LSPR measurement system 200b after introducing the target molecule to be detected. The LSPR measurement system 200a/b includes a light source 210 configured to illuminate test vehicles 220a/220b and transmit therethrough incident light 214, and a photodetector 230 configured to detect the transmitted light 238a/238b at a range of wavelengths. Unlike the SPR measurement system described with respect to FIG. 1 in which the detected light is reflected light, the LSPR measurement system of FIGS. 2A and 2B are configured to detect the target molecules from light 238a, 238b that is transmitted through the test vehicles 220a/220b.

Referring to FIGS. 2A and 2B, the test vehicles 220a/220b includes a container 222 configured to hold a solution 232 and a substrate 224. The container 222 and the substrate 224 have interior surfaces 222S and 224S that are configured to come in contact with the solution 232 when present. At least a portion of the interior surface 222S and/or a portion of the interior surface 224S have a layer of metallic nanoparticles 228 formed thereon. In addition, at least a portion of the interior surface 222S and/or a portion of the interior surface 224S have capturing molecules, sometimes called ligands, 244 formed thereon. In some embodiments, capturing molecules 244 are immobilized to the interior surfaces 222S and/or 224S surface either directly (e.g., chemically bound) or indirectly (e.g., capture antibody). The capturing molecules 244 are adapted to capture specific target molecules 236 by chemically binding thereto. Referring to FIG. 2B, when target molecules 240 are introduced into the solution 232, at least some of the target molecules 240 chemically attach to the capturing molecules 244.

In operation, the incident polarized light 214 from the light source 210 that is transmitted through the test vehicle 200a prior to exposing the capturing molecules 244 to the target molecules 240 and the test vehicle 200b after exposing the capturing molecules 244 are compared to detect the presence of the target molecules 240. Without being bound to any theory, when the target molecules (or analyte) 240 are introduced to the test vehicle 200a, some of the target molecules 240 binds to the capturing molecules (or ligands) 244, thereby causing perturbations at the surface of the metallic nanoparticles 228 that induce a modification of the resonance conditions. The modification results in a change in absorbance that can be measured based on a difference in the transmitted light 238a that is transmitted through the test vehicle 200a prior to being exposed to the target molecules 240 and the transmitted light 238b that is transmitted through the test vehicle 200b after being exposed to the target molecules 240. The bound target molecules 240 cause an increase in the refractive index whose magnitude is proportional to the concentration of the bound target molecules 240. Thus, the bound target molecules 240 induce a change in absorbance that is detected via the photodetector 230 and analyzed by an analysis unit 248. Thus, the disclosed LSPR measurement system allows a quantitative measurement of the concentration of the target molecules 240.

It will be appreciated that, without being bound to any theory, the layer of metallic nanoparticles 228 of FIG. 2B have distinctly different optical response characteristics compared to the thin metal film of FIG. 2A. Under certain circumstances, nanoparticles of metal exhibit a stronger optical resonances compared to a thin film of metal. As a result, a plane wave impinging on a metallic particle (e.g., tens of nm) can be strongly "focused" into the particle, leading to a large electric field density in a region of few nanometers to few tens of nanometers around the particle, the size of which generally increases with increasing size of the particle. For instance, for a 40 nm gold nanoparticle, the region may extend up to 60 nm from the surface of the nanoparticle. Furthermore, without being bound to any theory, nanoparticles that are densely packed and/or regularly spaced apart can exhibit even further enhanced field intensities as a result of plasmon coupling between adjacent particles. Furthermore, by varying nanoparticle shape or geometry, the SPR frequency can be tuned over a broad spectral range. Thus, the ability to achieve intense local field intensities renders LSPR techniques more versatile compared to SPR techniques, according to various embodiments disclosed herein.

In the following, without loss of generality, the target molecule 240 to be detected can include a molecule such as amino acids, peptides, polypeptides, proteins, glycoproteins, lipoproteins, nucleosides, nucleotides, oligonucleotides, nucleic acids, sugars, carbohydrates, oligosaccharides, polysaccharides, fatty acids, lipids (e.g., lipid vesicles), hormones, metabolites, cytokines, neurotransmitters, antigens, allergens, antibodies, inhibitors, drug molecules, toxins, poisons, pesticides, bacteria, virus, radioisotopes, vitamins, amphetamines, deoxyribonucleic acid (DNA), ribonucleic acid (RNA), metal ions, residual chemicals in food such as antibiotics in meat, and contaminants in water, to name a few.

In the following, without loss of generality, the capturing molecule 244 can include a suitable molecule that is adapted to capturing the target material to be detected, including antigens, antibodies, proteins, peptides, deoxyribonucleic acid (DNA), ribonucleic acid (RNA), peptide nucleic acid (PNA), enzymes, hormones or hormone receptors, to name a few.

In the following, without loss of generality, metallic nanoparticles 228 can include metallic elements such as aluminum (Al), bismuth (Bi), cobalt (Co), copper (Cu), gold (Au), iron (Fe), indium (In), molybdenum (Mo), nickel (Ni), chromium (Cr), silver (Ag), palladium (Pd), platinum (Pt), ruthenium (Ru), rhodium (Rh), tin (β-Sn), tantalum (Ta), titanium (Ti), tungsten (W) and zinc (Zn), to name a few. The metallic nanoparticles can additionally include oxides or nitrides of metallic elements that are metallic, such as, for example, TiN, TaN, TaCN, and $RuO_2$, to name a few. The metallic nanoparticles can additionally include semiconductor materials having sufficiently high doping concentration such that their properties are metallic. For example, highly-doped semiconductor nanoparticles can include semiconductor materials such as silicon (Si), germanium (Ge), tin (α-Sn), gallium arsenide (GaAs), indium arsenide (InAs), cadmium selenide (CdSe), cadmium sulfide (CdS), cadmium telluride (CdTe), zinc sulfide (ZnS), zinc selenide (ZnSe) and lead sulfide (PbS), to name a few. Metal oxides, metal nitrides, and semiconductor nanoparticles that have metallic properties can have, for example, a carrier density (e.g., electron density) which exceeds $1\times10^{18}/cm^3$.

In FIG. 2B, for illustrative purposes only, the metallic nanoparticles 228 are depicted as having a spherical shape. However, the metallic nanoparticles 228 can have various other shapes including, for example, spheroidal, ellipsoidal, pyramidal, rod-like, wire-like, polygonal, and multi-podded. In addition, the metallic nanoparticles 228 can have voids enclosed therein or have a core-shell structure in which at least the shell of the core-shell structure comprises a metal or a metallic oxide or semiconductor described above.

Polymer-Based LSPR Test Vehicles Having Substrates Coated with Nanoparticles

Outer Case and Sample Container

Referring to FIGS. 3A-3D, an LSPR test vehicle 300 is illustrated according to an embodiment. Referring to FIGS. 3A and 3B, the test vehicle 300 includes an outer case 304 comprising a front portion 310 and a rear portion 320 that are configured to enclose a container 350. The test vehicle 300 is configured to receive incident light 314 traveling in an x-direction on a front side and pass transmitted light 338 from an opposite side.

In various embodiments, at least portions of the outer case 304 and the container 350 are made using an optically transparent material, e.g., a polymeric material, that is transparent within the visible wavelengths of light. As described herein, visible light refers to photons of light having a wavelength between about 380 nm to about 1100 nm. In some embodiments, at least portions of the outer case 304 are made using a material that is optically opaque to visible light. In some embodiments, some portions of the container 350 are made using an opaque material. In some embodiments, at least portions of the sides of the outer case 304 and the container 350 through which the incident light 314 enters and exits the test vehicle can be made using a material that is optically transparent so as to allow light to pass. In some embodiments, at least portions of the sides of the outer case 304 and the container 350 through which the incident light 314 enters and exits the test vehicle can be made using a material that is optically transparent so as to pass light through the test vehicle. The remaining portions can be also made using a transparent material, an opaque material, or both. In some embodiments, at least portions of the sides of the container 350 through which the incident light 314 enters and exits the test vehicle can be made using a transparent material, while the outer case 304 is substantially entirely made using an opaque material. The remaining portions of the container 350 can be also made using a transparent material, an opaque material, or both.

In some embodiments, the front portion 310 of the outer case 304 has a light receiving window 340 adapted for passing the incident light unhindered. In the illustrated embodiment, the light receiving window 340 is a slot, an indentation or a notch from which the material of the outer case 304 is removed or carved out therefrom to maximize transmission of light therethrough. In other embodiments, the light receiving window 340 can be in the form of a transparent or a partially transparent window. In yet other embodiments, the light receiving window 340 can be in the form of an optical filter configured to selectively pass greater fractions of certain wavelengths. While not shown, the rear portion 320 can have a light exiting portion that may be similar to and at least partially aligned with the light receiving window 340 in the x-direction.

Referring to FIGS. 3B-3D, the container 350 has a light receiving window 354 for receiving the incident light 314 unhindered. In the illustrated embodiment, the light receiving window 314 is an optically transparent window whose material and thickness is optimized to maximize transmission of light therethrough. For example, in embodiments where substantially the entire container 350 is made using an optically transparent material, the light receiving window 314 can have a thickness that is lower than remaining portions of the container 350. In yet other embodiments, the light receiving window 314 can be in the form of an optical filter configured to selectively pass greater fractions of certain wavelengths. In yet other embodiments, the light receiving window 314 can be in the form of an optical lens configured to focus the light passing therethrough. While not shown, the container 350 can have a light exiting window 358 that may be similar to and at least partially aligned with the light receiving window 354 in the x-direction.

In the illustrated embodiment, the light receiving window 354 and the light exiting window 358 are recessed relative to each other such that a distance between them are reduced compared to the remaining front and rear surfaces of the container 350. Having such configuration can be advantageous for optimizing the path of light and/or optimizing, e.g., reducing the overall volume of the solution that is held by the container 350.

In some embodiments, the container 350 is configured as a cuvette that comprises a tubular inner cavity and is configured to hold a liquid sample. In the illustrated embodiment, the container 350 and the outer case 304 has a square cross section. However, it will be appreciated that the container 350 and/or the outer case 304 can have other suitable cross-sectional shapes, such as, for example, circular cross section. The container 350 can have lateral dimensions that have dimensions that allow for easy calculation of various parameters, such as, for example 10 mm across a length in the x-direction that is traversed by the light beam.

Polymer-Based Substrates for Target Molecule Detection

Still referring to FIGS. 3B-3D the container 350 is configured to hold one sample substrate 362 or a plurality of sample substrates 360a, 360b, and 360c. In the illustrated embodiment of FIG. 3D, the container 350 holds three substrates 360a, 360b and 360c. However, in other embodiments, the container 350 can hold fewer or more substrates. Each substrate 362, 362a-362c has a handle region 362 and an analysis region 368. Each substrate has a front side facing the incident light 314 and a rear side facing the transmitted light 338. At least portions of the sample substrates 362, 362a-362c are formed using a transparent material, e.g., a transparent polymeric material.

Referring back to FIGS. 3A and 3B, the front portion 310 of the outer case has a front opening 330 and the rear portion 320 has a rear opening 334. In addition, referring to FIGS. 3B-3D, the substrates 362, 362a-362c also have openings 364 in the handle region 362. The inventors have found that having such openings can be beneficial for reducing the number of bubbles that may form in a gap between a substrate and an adjacent inner surface of the container 350, or a gap between adjacent substrates when multiple substrates are present. Under some circumstances, bubbles that form in such gaps rise up to the openings, where they may be punctured, thereby being reduced or eliminated. In some embodiments, the front and rear openings 330 and 334 and the openings 364 are substantially aligned both laterally and vertically, which the inventors have found to maximize the effectiveness in minimizing bubbles.

As described herein, an optically transparent material in the visible wavelengths refers to a material which transmits at least about 80% of an incident light at the visible wavelengths. Without loss of generality, transparent polymeric materials that can be used for any or all of the case, the container and the substrates include polycarbonate (PC), polyethylene terephthalate, polymethyl methacrylate, triacetyl cellulose (TAC), cyclic olefins, polyethylene terephthalate, polyarylate, polyethylene terephthalate, polybutylene terephthalate, polyimide or combinations thereof. Transparent non-polymeric or inorganic materials that can be used include silicon oxide-based materials (e.g., amorphous silica or quartz) or aluminum oxide-based materials (e.g., sapphire).

Target Molecule Detection Via Nanoparticles and Capturing, Molecules

Referring to FIGS. 3E and 3F, the container 350 is configured to receive and hold a solution 332 therein. At least portions of the front and rear side surfaces 368F. 368R of the analysis region 368 of the substrate 360 have a layer of metallic nanoparticles 328 formed thereon. In addition, at least portions of the front and rear side surfaces of the analysis region 368 have a layer of capturing molecules 344 formed thereon. The capturing molecules 344 may be immobilized. In some embodiments, the substrate 360 has an uncoated portion 362 that does not have one or both of metallic nanoparticles 328 and the layer of capturing molecules 344 formed thereon. The capturing molecules 344 are adapted to capture specific target molecules by chemically binding thereto. Referring to FIG. 3E, when target molecules 340 are introduced into the solution 332, at least some of the target molecules 340 chemically attach to the capturing molecules 344. While the illustrated embodiment only illustrate the nanoparticles 328 and the capturing molecules 344 formed on the surface of the analysis region 368 of the substrate 360, in other embodiments, at least portions of the interior surfaces of the container 350, e.g., portions of the interior surfaces of the light receiving window 354 and light exiting window 358, can also have the nanoparticles 328 and the capturing molecules 344 formed thereon.

Referring to FIGS. 3E and 3F, in operation, the incident light 314 is transmitted through the test vehicle 300a (FIG. 3E) before exposing the substrate 360 having the capturing molecules 344 to the target molecules 340, and through the test vehicle 300b (FIG. 3F) after exposing the substrate 360 to the target molecules 340. Absorbance of the light though the test vehicles 300a and 300b are then compared to detect the presence of the target molecules 340. In the illustrated embodiment, the incident light 314 is directed to the analysis region 368 of surface 360 such that substantially all of the incident light 314 exits the analysis region 368 as transmitted light 338a/b without being substantially reflected. In some embodiments, the incident light 314 is directed at an angle that is substantially perpendicular to the surface of the analysis region receiving the incident light 314. Without being bound to any theory, some of the target molecules 340 bind to the capturing molecules 344, thereby causing perturbations at the surface of the metallic nanoparticles 328 that induce a modification of the resonance conditions, which in turn results in a change in absorbance that can be measured based on a difference in the transmitted light 338a that is transmitted through the test vehicle 300a prior to being exposed to the target molecules 340 and the transmitted light 338b that is transmitted through the test vehicle 300b after being exposed to the target molecules 340. The bound target molecules 340 cause an increase in the refractive index whose magnitude is proportional to the concentration of the bound target molecules 340. Thus, the bound target molecules 340 induce a change in absorbance that can be detected for quantitative analysis, described infra.

Absorbance and Absorbance Difference Spectra

Figure 4B:
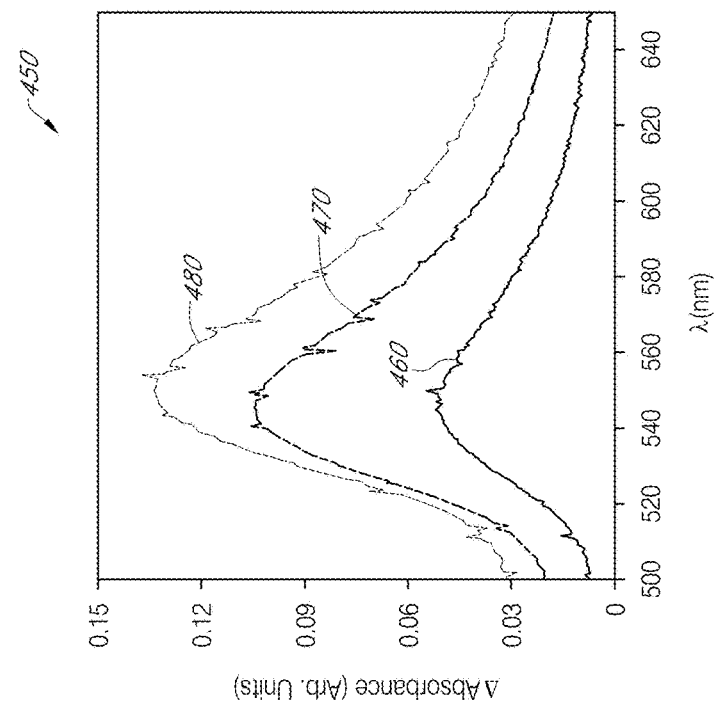
FIG. 4B illustrates absorbance difference spectra obtained from polymer-based LSPR test vehicles having one, two and three substrates, according to embodiments.
Figure 4A:
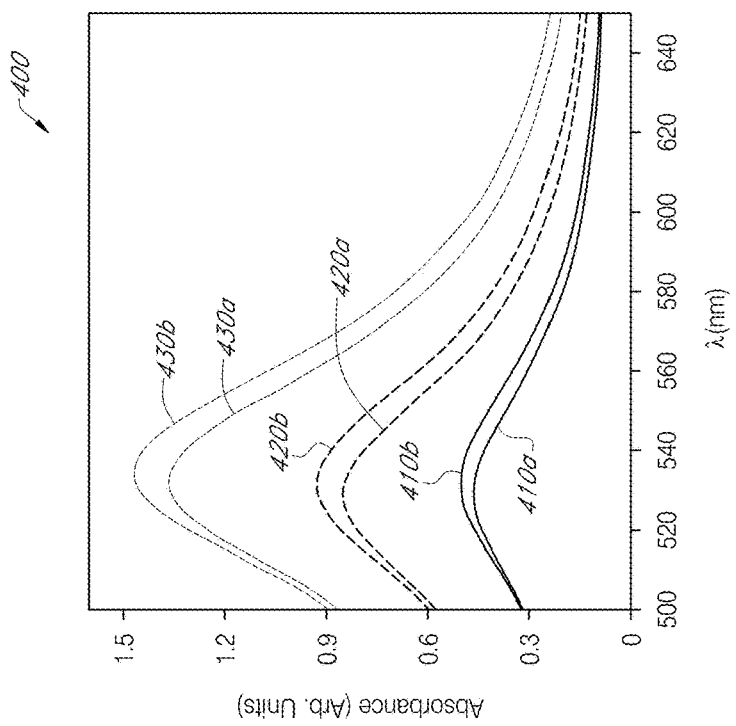
FIG. 4A illustrates absorbance spectra obtained from polymer-based LSPR test vehicles having one, two and three substrates, according to embodiments.

FIG. 4A is a graph 400 illustrating a set of absorbance spectra taken using LSPR test vehicles similar to those described above with respect to FIGS. 3A-3F, using an LSPR measurement system similar to those described above with respect to FIGS. 2A and 2B, according to embodiments. The y-axis of the graph 400 represents the measured absorbance and the x-axis represents the wavelength ($\lambda$) at which the absorbance is measured. The illustrated absorbance spectra 410a, 420a and 430a represent, for example, measured absorbance values of the test vehicle having one, two and three substrates, respectively, where each substrate is arranged similar to the test vehicle described above with respect to FIG. 3E, where each of the substrates having nanoparticles formed thereon are immersed in a solution and have formed thereon capturing molecules, prior to introduction of the target molecules. The illustrated absorbance spectra 410b, 420b and 430b represent, for example, measured absorbance values of the one, two and three substrates of, respectively, where each substrate is arranged similar to the test vehicle described above with respect to FIG. 3F, where each of the substrates having nanoparticles formed thereon are immersed in a solution and have formed thereon capturing molecules, after introduction and attachment of the target molecules to the capturing molecules. In the illustrated absorbance spectra 410a, 420a and 430a, each of the substrates have about the same area of coverage of nanoparticles and capturing molecules in the analysis region(s) (368, 368a, 368b, and 368c in FIGS. 3B-3D). In addition, in the illustrated absorbance spectra 410b, 420b and 430b, each of the substrates are subjected to about the same concentration of target molecules in the solution in which the analysis regions are immersed.

FIG. 4B is a graph 450 illustrating a set of absorbance difference spectra that can be obtained based on the set of absorbance data set similar to that of FIG. 4A, according to embodiments. The y-axis of the graph 450 represents a difference in absorbance values between the measured absorbance before and after subjecting the substrates to a concentration of target molecules in the solution in which the analysis regions of the substrates are immersed. The x-axis represents the wavelength ($\lambda$) at which the absorbance is measured. The illustrated absorbance difference spectra 460, 470 and 480 represent, for example, measured difference in absorbance values prior to and after subjecting the substrate(s) to the target molecules at various wavelengths for the test vehicle having one, two and three substrates, respectively. That is, the absorbance spectra 460, 470 and 480 can represent, for example, difference in intensities of light before the substrate(s) are subjected to the target molecules (similar to 410a, 420a and 430a, for example), and after the substrate(s) are subjected the target molecules (similar to 410b, 420b and 430b, for example). As illustrated, the difference values of the absorbance difference spectra 460, 470 and 480 increase proportionally with the number of substrates.

In some practical implementations, instead of taking spectra of absorbance or changes in absorbance as shown in FIGS. 4A and 4B, it may be more practical to measure the absorbance or changes in absorbance (Δ Absorbance) at a particularly chosen wavelength, (e.g., a peak wavelength). FIG. 4C is a graph 500 illustrating, in the y-axis, a change in absorbance resulting from exposing substrate(s) to target molecules, measured at a single wavelength (e.g., a peak wavelength), as a function of number of substrates (x-axis) disposed in the test vehicle. Similar to as described above with respect to FIG. 4B, the magnitude of change in absorbance increases proportionally to the number of substrates through which the light passes through. In addition, because the change absorbance intensity change is directly proportional to a corresponding change in refractive index, the y axis can interchangeably represented as a change in Δ Refractive Index.

Figure 5:
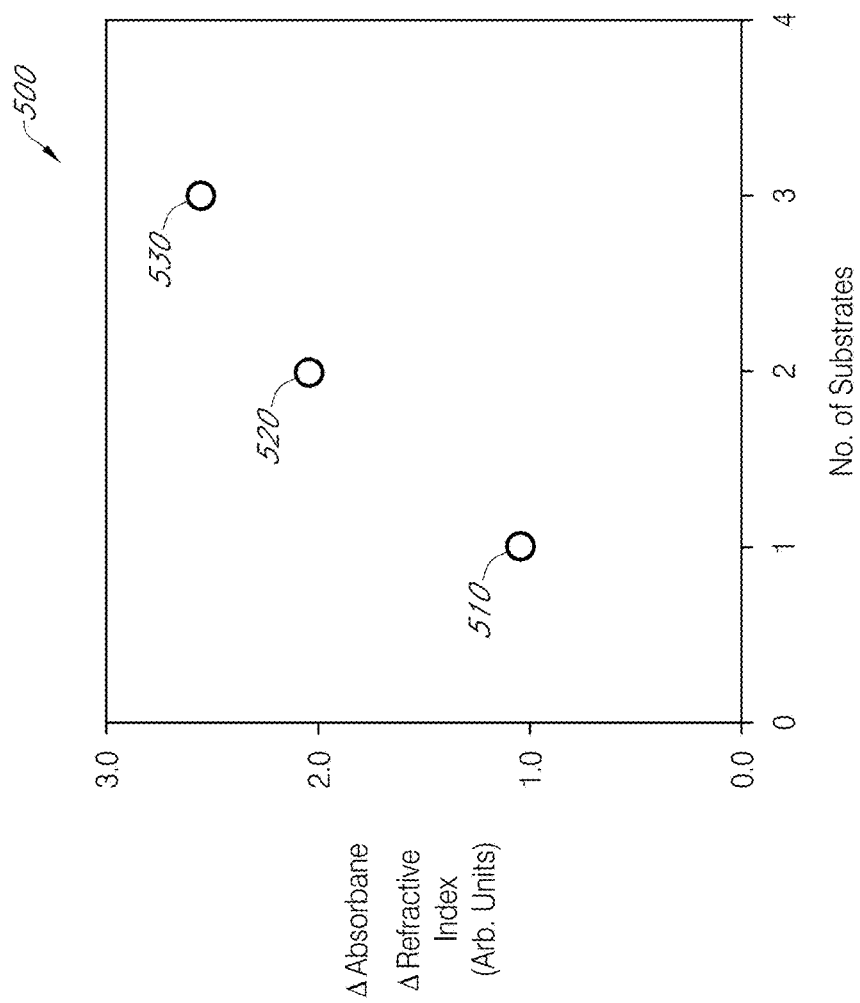
FIG. 5 illustrates absorbance difference and refractive index difference obtained from polymer-based LSPR test vehicles as function of number of substrates, according to embodiments.

Thus, as illustrated, in FIGS. 4A and 4B, the absorbance spectra 410b, 420b and 430b of LSPR test vehicles, whose substrate(s) has nanoparticles and capturing molecules formed thereon to target molecules, display increased absorbance values after exposing the substrate(s) to target molecules compared to the respective absorbance spectra 410a, 420a and 430a prior to exposing the substrate(s) to the target molecules. The magnitude of increase in absorbance values is proportional to, among other things, the surface concentration of the attached target molecules. Thus, based on known values of the nanoparticle surface density and the capturing molecule surface density, and based on the measured difference in absorbance before and after exposing the substrate(s) to the target molecules, the concentration of target molecules in the solution can be determined. In addition, as described in FIGS. 4B and 5, using test vehicles configured to hold a plurality of substrates as illustrated in FIG. 3D, the detection sensitivity (e.g., signal to noise ratio) of the target molecules can be enhanced, because absorbance increases proportionally to the number of substrates.

Test Vehicles Based on Attenuated Total Internal Reflection

It is known that when a light beam is passes through a first medium (e.g., glass) having a first refractive index $n_1$ and directed into a second medium (e.g., liquid or air) having a second refractive index $n_2$ that is lower than $n_1$, the light beam bends at an interface between the first and second media away from a normal having a direction perpendicular to the interface. The magnitude of bending of the light beam is governed by Snell's Law, which states that $n_1 \times \sin \theta_1 = n_2 \times \sin \theta_2$, where $n_1$ and $n_2$ are refractive indices of the first and second media, respectively, $\theta_1$ represents a first angle of the incident beam within the first medium with respect to the normal, and $\theta_2$ represents a second angle of the refracted beam within the second medium with respect to the normal.

When the light beam traveling through the first medium strikes the interface between the two media at a sufficiently high angle, known as a critical angle $\theta_c$, its refraction direction becomes parallel to the interface (90 degrees relative to the normal), and at larger angles it is reflected entirely back into the first medium. This condition is known as total internal reflection. When a collimated light beam propagating through a light-guiding structure, e.g., a fiber, comprising a first medium having a first index, reaches an interface, at an angle greater than $\theta_c$, between the structure and an external medium, such as a material formed on the surface of the structure and comprising a second medium having a second index lower than the first index, the light beam can be guided through the structure under total internal reflection mode by undergoing a series of total internal reflections at the interface between the two media. The number of reflections may be varied by varying the angle of incidence. The technique is sometimes referred to as attenuated total internal reflection, or ATR. In some embodiments of the LSPR test vehicles, LSPR measurement methods and LSPR measurement systems disclosed herein, ATR can be advantageously be employed, as described in the following.

Polymer-Based Light Guiding Structures for LSPR Measurements Based on ATR

FIG. 6A illustrates a polymer-based LSPR test vehicle 600 configured to utilize attenuated total reflection (ATR). The test vehicle 600 includes a light-guiding structure 660 having a length L extending in a z-direction and having a first index of refraction $n_1$. The illustrated portion of the structure 660 may represent, for example, an analysis region similar to the analysis region 368 of FIGS. 3A-3F and include optically transparent material, e.g., an optically transparent polymeric material.

In some embodiments, the light-guiding structure 660 has a surface or a plurality of surfaces. The structure 660 is illustrated as having a first surface 660S1 and a second surface 660S2 that oppose each other and are configured to reflect a beam of light in the ATR mode. In some embodiments, the first and second surfaces 660F and 660R represent different portions of a single surface, as illustrated infra with respect to FIGS. 6B-6C.

At least portions of the first and second surfaces 660S1 and 660S2 have a layer of metallic nanoparticles 628 formed thereon. In addition, at least portions of the first and second surfaces 660S1 and 660S2 have capturing molecules 644 formed thereon. The capturing molecules 644 are adapted to capture specific target molecules by chemically binding thereto.

Similar to the test vehicle 300 described above with respect to FIGS. 3A-3F, the surfaces 660S1 and 660S2 are configured to come in contact with a solution 632, which may be held in a container in which the structure 660 may be at least partially immersed, in a similar manner as described with respect to the substrate 360 of FIGS. 3A-3F. The solution 632, with or without having target molecules dissolved therein, has a second refractive index $n_2$, which is lower than the first refractive index $n_1$ of the structure 660. Similar to the capturing molecules described above with respect to FIGS. 3E-3F, when target molecules 640 are introduced into the solution, at least some of the target molecules 640 chemically attach to the capturing molecules 644.

Still referring to FIG. 6A, unlike the test vehicle described supra with respect to FIGS. 3E and 3F in which light beams are transmitted through a substrate in a single pass, an incident light beam 614, e.g., a light beam, enters the light-guiding structure 660 through an end surface 660S3 and travels generally along the z-direction, corresponding to the lengthwise direction of the structure 660. The light beam 614 is directed toward one of the surfaces 660S1 or 660S2 of the structure 660 at an angle θ relative to a normal (x-axis) that is greater than a critical angle $\theta_c$ for attenuated total internal reflection (ATR) condition as described above, such that the light beam 614 does not exit through the one of the surfaces 660S 1 or 660S2, but instead is internally reflected back into the interior of the structure 660 towards the other of the surfaces 660S1 or 660S2. The internal reflection event can be repeated a plurality of times by independently choosing the values of $n_1$, $n_2$, L and θ, such that a suitable number of internal reflection events that may be suitable for a given system may occur.

It will be appreciated that, in some implementations, the light beam 614, which may be collimated, is directed towards one of the surfaces 660S1 or 660S2 of the structure 660 such that the ATR condition is satisfied as descried above. In some other implementations, the light beam 614 may be uncollimated or partially collimated as it enters a first end of light-guiding structure 660. Upon entry, some photons satisfy the ATR condition and are total internally reflected thereby reaching the second end of the light-guiding structure 660, while other photons that do not satisfy the ATR conditions are transmitted through or diffuse-scattered at one of the surfaces 660S1 or 660S2. In this way, in some implementations, the polymer-based LSPR test vehicle 600 "self-selects" light beams satisfying the ATR conditions, obviating the need for a high degree of pre-collimation of the light beam 614.

Without being bound to any theory, although the light beam 614 is totally internally reflected, the reflected light generates a restricted electromagnetic field adjacent to the surfaces 660S1 and 660S2 such that an evanescent field is created, which decays exponentially in intensity away from the surfaces 660S1 and 660S2 in the x-direction. A characteristic total reflection evanescence decay length, e.g., a l/e decay length in amplitude of the field wave, which can be denoted by $d_o$ (not shown) may extend, for example, about ⅓ of the wavelength of the incident light, e.g., a hundred to a few hundred nanometers, for instance about 200 nm.

In the LSPR test vehicle 600 of FIG. 6A under the ATR condition according to embodiments, the free electrons at the surface of the metallic nanoparticles 628 can be excited by the evanescent field, thereby inducing a localized surface plasmon resonance (LSPR). Without being bound to any theory, because of the exponential falloff of evanescent field intensity within $d_o$, the excitation of the surface free electrons is restricted to a region, also known as an LSPR field decay length ($\lambda_o$) that is typically less than 100 nanometers in thickness (e.g., ~20 nm). Because excitation of the metallic nanoparticles 628 can be relatively localized to a relatively thin region, and because the light beam undergoes a plurality of internal reflection events, a much higher signal-to-noise ratio can be achieved in using the LSPR test vehicle 600 compared to many other SPR techniques.

Thus, according to the embodiments disclosed herein, by comparing light beams that are transmitted through the light-guiding structure 660 under ATR conditions before and exposing the capturing molecules 644 to target molecules 648, the presence of the target molecules in the solution 632 can be detected based on perturbations caused by target molecules 640 that bind to the capturing molecules 644, at the surface of the metallic nanoparticles 628 that induce a modification of the resonance conditions. The modification of the resonance conditions in turn results in a change in absorbance that can be measured based on a difference in the transmitted light 638 that is transmitted through the test vehicle 600 before and after exposing the structure 660 to the target molecules 640 in a similar manner as described above with respect to FIGS. 3A-3F, but at a higher sensitivity and higher signal-to-noise level.

Figure 6B:
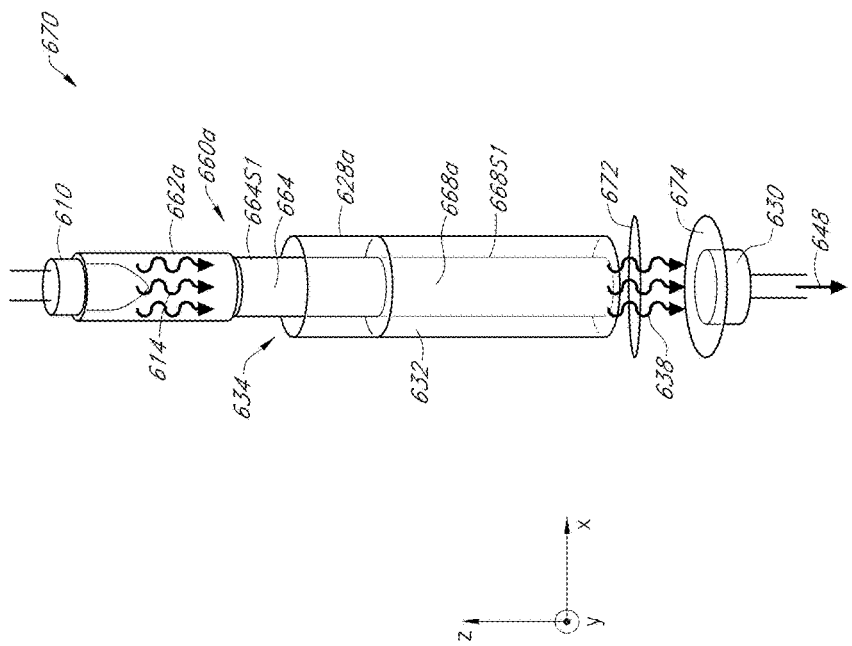
FIGS. 6B-6D are different configurations of polymer-based ATR LSPR test vehicles, according to embodiments.
Figure 6C:
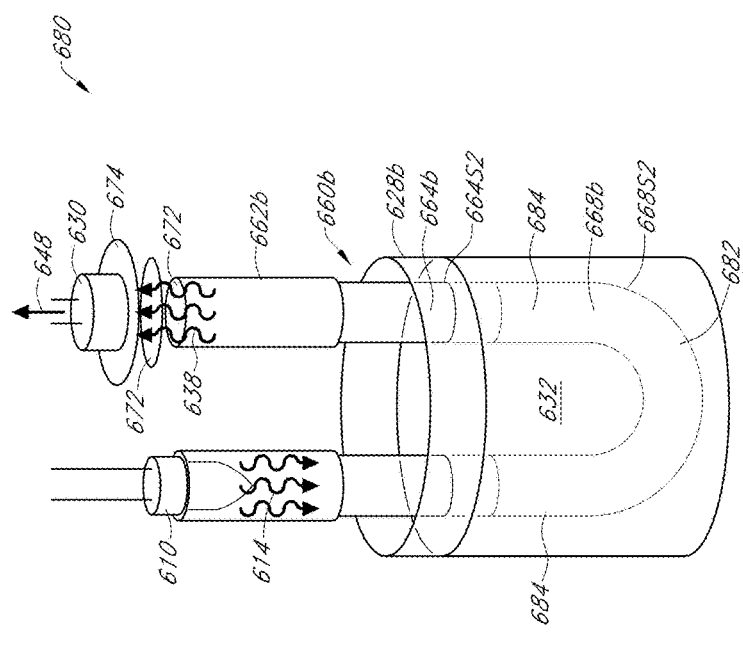
Figure 6D:
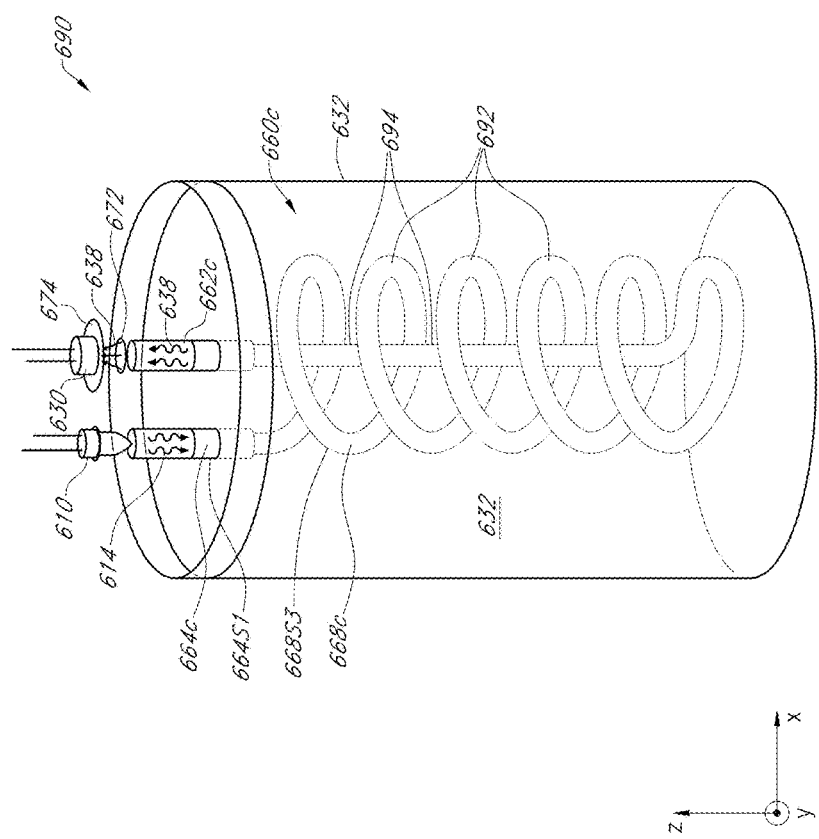

Configurations of Polymer-Based Light Guiding Structures for LSPR Measurements Based on ATR FIGS. 6B, 6C and 6D illustrate polymer-based LSPR test vehicles 670, 680 and 690, respectively, that are configured to utilize attenuated total reflection (ATR), in a manner similar to as described above with respect to FIG. 6A. In particular, FIGS. 6B-6D illustrate test vehicles having analysis regions that are uniformly and continuously coated with metallic nanoparticles and capturing molecules. It will be understood that the analysis regions of test vehicles illustrated in FIGS. 6B-6D represent embodiments that can be used as stand-alone analysis region for a given test vehicle. In addition, the analysis regions and various regions or portions thereof can be used in combinations or repeating.

Each of the test vehicles 670, 680 and 690 includes a light guiding structure 660a, 660b, and 660c, respectively, each comprising a respective analysis region 668a-668c having a first index of refraction $n_1$. Each of the light guiding structures 660a-660c has a first end and a second end and the respective analysis region 668a-668c between the first and second ends, each of which comprises an optically transparent material, e.g., an optically transparent polymeric material. Each of the analysis regions 668a-668c has a respective analysis region surface 668S1, 668S2 and 668S3 that comprises the transparent polymeric material. In the illustrated embodiment, the transparent polymeric material has the first index of refraction $n_1$ and each of the analysis region surfaces 668S1-668S3 is configured to reflect a beam of light in the ATR mode as described above with respect to FIG. 6A.

Similar to as described above with respect to the surfaces 660S1 and 660S2 of the light guiding structure 660 described above with respect to FIG. 6A, in the illustrated embodiments of FIGS. 6B-6D, at least portions of the analysis region surfaces 668S1-668S3 have a layer of metallic nanoparticles 628 (not shown for clarity) formed thereon. In addition, at least portions of the analysis region surfaces 668S1-668S3 have capturing molecules 644 (not shown for clarity) formed thereon. The capturing molecules 644 are adapted to capture specific target molecules by chemically binding thereto.

Still referring to FIGS. 6B-6D, any one or more of the light guiding structures 660a-660c can have an uncoated portion 664a, 664b, and 664c comprising the same transparent polymeric material as the analysis regions 668a-668c and having respective surfaces 664S1, 664S2 and 664S3 that do not have one or both of metallic nanoparticles 628 and the layer of capturing molecules 644 formed thereon. In addition, any one or more of the light guiding structures 660a-660c can have a respective light guiding portion 662a, 662b and 662c comprising the same transparent polymeric material as the analysis regions 668a-668c and disposed near at least one of the first and second ends of the light guiding structures.

Still referring to FIGS. 6B-6D, each of the test vehicles 670, 680 and 690 has a respective container 628a, 628b and 628c that is configured to hold a liquid solution 632 therein. The liquid is adapted to dissolving the target molecules 648 (not shown) as described above with respect to FIG. 6A. When the liquid 632 is present, each of the light guiding structures 660a-660c is configured such that at least portions of the analysis regions 668a-668c can be immersed in the liquid 632.

As described above with respect to FIG. 6A, each of the analysis region surfaces 668S1-668S3 is configured to come in contact with the solution 632 in the container 628a-628c. The solution 632, with or without having the target molecules dissolved therein, has a second refractive index $n_2$, which is lower than the first refractive index $n_1$ of the analysis regions 668a-668c. Similar to the capturing molecules described above with respect to FIGS. 3E-3F, when target molecules 640 (not shown) are introduced into the solution 632, at least some of them chemically attach to the capturing molecules 644 (not shown), such that a change in absorbance of light is induced.

Still referring to FIGS. 6B-6D, in operation, each of the test vehicles 670, 680 and 690 is configured such that an incident polarized light beam 614 emitted by a light source 610 is received at a first end of the light guiding structures 660a, 660b and 660c, and further configured to at least partially transmit light though the respective light guiding structures 660a, 660b and 660c. Each of the test vehicles 670, 680 and 690 is further configured such that the transmitted light is emitted at a second end of the light guiding structures 660a, 660b and 660c, to be detected using a detector 630. In some embodiments, there may be one or more lenses 672 and/or one or more optical filters 674 disposed between the second end of the light guiding structures and the detector 630 to focus light and/or selectively filter light traveling therethrough.

Each of the test vehicles 670, 680 and 690 is configured such that the light transmitted through the light guiding structures 660a, 660b and 660c is guided between their first and second ends under an attenuated total internal reflection (ATR) condition as described above. That is, because the second refractive index $n_2$ of the solution 632 is lower than the first refractive index $n_1$ of the analysis regions 668a, 668b and 668c, a light beam traveling through the light guiding structures 660a-660c and reaching a respective surface 668S1, 668S1 and 668S3, which forms an interface with the solution 632, at a certain angle does not exit through the surface 668S1, but instead is internally reflected back into the interior of the light guiding structures 660a-660c towards an opposite surface. In particular, a light beam reaching the interface and forming an angle θ relative to a normal of the surface 668S1, 668S2 and 668S3, at the point of light impingement, that is greater than a critical angle $\theta_c$ will satisfy the attenuated total internal reflection (ATR) condition as described above. The internal reflection event can be repeated a desired number of times by independently choosing the values of $n_1$, $n_2$, θ and the path length of the light such that a suitable number of internal reflection events that may be suitable for a given system may occur.

Referring to FIG. 6B, the test vehicle 670 comprising a light guiding structure 660a that is configured to receive incident light 614 from one side and to collect the transmitted light 638 from the opposite side of the test vehicle 670 in the vertical direction is illustrated, according to one embodiment. The test vehicle 670 includes the light guiding portion 662a, the uncoated portion 664a and the analysis portion 668a that are arranged in a substantially co-linear column configuration. At least the analysis portion 668a is formed using a polymeric material such that the analysis region surface 668S1 has a polymeric surface that is adapted for forming a layer of metallic nanoparticles (not shown for clarity) and for attaching capturing molecules (not shown for clarity) thereon, where the capturing molecules are adapted to capture specific target molecules. At least a portion of the analysis portion 668a is configured to be immersed in the solution 632. The solution is adapted to dissolve therein the target molecules to be detected. Advantageously, the substantially co-linear configuration of the light guiding structure 660a is suited for LSPR measurement systems in which the length of the light source 610 and the light detector 630 are disposed on opposite sides of the light guiding structure 660a in the direction of light travel.

It will be appreciated that various dimensions of the various portions of the light guiding structure 660a can be adjusted for desired detection characteristics. For example, the length of the analysis region 688 in the z-direction, a diameter of the analysis region 688 in the y or z directions, and the index of refraction n1 of the polymeric material of the light guiding structure 660a can be chosen, e.g., based on the number of total internal reflections desired based on other physical constraints such as, for example, size of the container 628a, which can be chosen based on the availability of the amount of the target molecules that can be dissolved in the container 628a the index $n_2$ of refraction of the solution 632, and physical constraints of the nanoparticle coating apparatus and process, as described infra, to name a few.

In the illustrated embodiment of FIG. 6B, various portions of the light guiding structure 660a including at least the analysis portion 668a has a cross-sectional shape (in the y-z plane) that is substantially circular. However, possible embodiments are not so limited. For example, cross-sectional shapes that are polygonal (triangular, square, rectangular, pentagonal, hexagonal, octagonal, etc.), oval or other suitable shapes are possible.

In the illustrated embodiment of FIG. 6B, various portions of the light guiding structure 660a including at least the analysis portion 668a of the light guiding structure 660a does not deviate substantially from being linear in the light traveling direction (z-direction). That is, at least the analysis portion 668a of the light guiding structure 660a does not have a substantial curvature, flection, arc, bend, bow, twist, loop or turn which deviates away from the z-direction. In the following, with respect to FIGS. 6C and 6D, embodiments having such deviations from linearity are described.

Referring to FIG. 6C, the test vehicle 680 comprises a light guiding structure 660b having at least one curvature portion 682. Unlike the light guiding structure 660a of FIG. 6B, the light guiding structure 660b of the test vehicle 680 is configured to receive an incident light 614 from one side (e.g., the top) of the test vehicle 680 and to emit a transmitted light 638 to the same vertical side of the test vehicle 680, according to one embodiment.

Similar to the test vehicle 670 of FIG. 6B, at least the analysis portion 668b of the test vehicle 680 is formed using a polymeric material such that the analysis region surface 668S2 has a polymeric surface that is adapted for forming a layer of metallic nanoparticles (not shown for clarity) and for attaching capturing molecules (not shown for clarity) thereon, where the capturing molecules are adapted to capture specific target molecules. Also similar to FIG. 6B, at least a portion of the analysis portion 668b is configured to be immersed in the solution 632 that is adapted to dissolve the target molecules.

Unlike FIG. 6B, the test vehicle 680 has the light guiding portions 662b formed at each of the light receiving end and the light emitting end, and both the light receiving end and the light emitting end are configured to be placed outside the solution 632. Also unlike FIG. 6B, at least the analysis portion 668b of the light guiding structure 660b deviate substantially from being linear and include at least one curvature portion 682. In the illustrated embodiment, the curvature portion 682 includes a U-shaped bend region such that the light propagation direction is reversed from a downward direction towards an upward direction. As a result, the total-internally reflected light 672 exiting from the light detection end of the light guiding structure 660b is the same vertical side as the light receiving end of the light-guiding structure 660b, unlike the light guiding structure 660a of FIG. 6B. Advantageously, the nonlinear configuration of the light guiding structure 660b can be suited for LSPR measurement systems in which the light source 610 and the light detector 630 are disposed on opposite sides of the light guiding structure 660a in the direction of light travel.

For illustrative purposes only, the analysis region 668b, which includes a single curvature portion 682 comprising a U-shaped bend region, is illustrated. However, it will be appreciated that embodiments described herein are not so limited and a plurality of curvature portions 682 can be included as part of the analysis region 668b. For example, the analysis region 668b can include a plurality of curvature portions 682 having alternating concave and convex U-shaped bend regions that are connected in series to increase the overall effective length of the analysis region 668b.

Furthermore, each curvature portion 682 can include other shapes of curvatures. For example, the curvature portion 682 can include one or more of a flection, arc, bend and bow, among other curvature shapes, such that the light is directed away from the original traveling direction (downward direction) and towards a different direction. In addition, such curvature can be optimized to have a radius of curvature chosen to achieve the desired ATR absorption signal or signal-to-noise ratio.

In addition, similar to as described above with respect to FIG. 6B, the cross-sectional shape of the various portions of the light guiding structure 660a can have other shapes in addition to the illustrated circular shape, such as a polygonal (triangular, square, rectangular, pentagonal, hexagonal, octagonal, etc.), oval or other suitable shapes.

Referring to FIG. 6D, the test vehicle 690 comprises a light guiding structure 660c having a plurality of winding portions 692 that is configured to receive incident light 614 from one side and collect the transmitted light 638 from the same vertical side of the test vehicle 680, according to one embodiment.

Similar to the test vehicle 680 of FIG. 6B, at least the analysis portion 668c of the test vehicle 690 is formed using a polymeric material such that the analysis region surface 668S3 has a polymeric surface that is adapted for forming a layer of metallic nanoparticles (not shown for clarity) and for attaching capturing molecules (not shown for clarity) thereon, where the capturing molecules are adapted to capture specific target molecules. Also similar to FIG. 6B, at least a portion of the analysis portion 668c is configured to be immersed in the solution 632 that is adapted to dissolve the target molecules. In addition, the test vehicle 690 has the light guiding portions 662c formed at each of the light receiving end and the light emitting end, and both the light receiving end and the light emitting end are configured to be placed outside the solution 632. Also similar to FIG. 6C, at least the analysis portion 668c of the light guiding structure 660c deviate substantially from being linear and include a plurality of winding portions 692. In the illustrated embodiment, the analysis region 668c includes a plurality of winding portions 692 in which the light propagation direction is continuously changed laterally in a spiral manner and vertically in a downward direction towards. The analysis region 668c additionally includes a light return portion path 694 connected to an end of the lower most winding portion 692 such that the light beam changes its path towards an upward direction to be transmitted at the emitting end. As a result, the total-internally reflected light 672 exiting from the light detection end of the light guiding structure 660c is the same vertical side as the light receiving end of the light-guiding structure 660b Advantageously, the winding configuration of the light guiding structure 660c can be suited for LSPR measurement systems in which the light source 610 and the light detector 630 are disposed on opposite sides of the light guiding structure 660b in the direction of light travel.

For illustrative purposes only, the analysis region 668c, which includes six winding portions 692 is, illustrated. However, it will be appreciated that embodiments described herein are not so limited and any desired number of winding portions 692 can be included as part of the analysis region 668c. Furthermore, while the illustrated light return path portion 694 is a relatively straight, embodiments are not so limited. For example, the return path can also contain a plurality of winding portions that have radius curvature that are smaller or larger than the winding portions 692 such that the path of light travel is increased even further.

Furthermore, each curvature portion 682 can include other shapes of curvatures. For example, the curvature portion 682 can include one or more of a flection, arc, bend and bow, among other curvature shapes, such that the light is directed away from the original traveling direction (downward direction) and towards a different direction. In addition, such curvature can be optimized to have a radius of curvature chosen to achieve the desired ATR absorption signal or signal-to-noise ratio.

In addition, similar to as described above with respect to FIG. 6B, the cross-sectional shape of the various portions of the light guiding structure 660a can have other shapes in addition to the illustrated circular shape, such as a polygonal (triangular, square, rectangular, pentagonal, hexagonal, octagonal, etc.), oval or other suitable shapes.

Plasma-Assisted Coating of Polymeric Substrates with Nanoparticles

Plasma processes find many applications in manufacturing industries including electronics, aerospace, automotive, steel, biomedical and toxic waste management, to name a few. Gas phase plasma is an electrically neutral mixture which includes neutral molecules, electrons, ions and radicals. A gas phase plasma can be generated when energy (e.g., RF or DC) is applied to a volume of gas in a chamber through one or more electrodes, which results in electrons gaining sufficient kinetic energy such that they collide with atoms or molecule of the volume of gas, leading to formation of the gas phase plasma which includes electrons, ions and radicals. As one example, when a volume of oxygen gas ($O_2$ plasma) is subjected to sufficient energy to initiate plasma generation, the plasma that is generated contains species such as electrons, oxygen radicals, $O_2$, $O_3$, $O^-$, $O^{2-}$, $O^+$, $O^{2+}$ and $O^{+2}$. Thus generated reactive radical species can be utilized to perform various chemical work and the ionized atom and molecular species can be utilized to perform various chemical and/or physical work via interactions with a target surface of an article, e.g., a substrate. In most gas-phase plasma processes, the reactive radical species and/or the ionized species come in contact with the target surface of an article to be modified.

In some plasma processes, referred to herein as liquid-based plasma processes, discharges are generated in a liquid or using the liquid as an electrode. In some liquid-based plasma processes, a discharge is created directly in the liquid between two electrodes that are both placed inside the liquid. For example, in a process called Solution Plasma Processing (SPP), two electrodes placed directly in a solution which may contain chemical agents, for example, precursors, and a high voltage is applied therebetween to cause a breakdown (e.g., arc) of the liquid. In some other liquid-based plasma processes, discharges are created above a liquid by using the liquid which serves as one of the electrodes and another electrode that is disposed outside (e.g., above) the liquid. The liquid serves as an electrode by having conductive ions dissolved therein and while being connected to an immersed electrode such that the discharge current is transported through the liquid by ions in the liquid. In yet other liquid-based plasma processes, discharges are created in bubbles and cavities inside a conductive liquid and therefore are completely surrounded by the liquid in which two electrodes are disposed. Thus, in prior art liquid-based plasma processes, a discharge is generated by application of energy to a volume of liquid itself using one or more conductive electrodes submerged inside the liquid.

In the following, a gas-phase plasma processing is disclosed in which an article to be processed is at least partially submerged, according to embodiments. Unlike other gas-phase plasma processes, the article to be modified does not come in direct contact with the gas-phase plasma. In addition, unlike other liquid-based plasma processes, the liquid does not come in direct contact with an electrode. Instead, deposition of a material (e.g., binder polymer) is caused or accelerated on a surface of the article by a gas-phase plasma that is generated above a liquid composition in which the surface is immersed.

In embodiments, plasma processing methods relate to coating an article with a layer of materials, e.g., a polymer layer and/or a nanoparticle layer. The method includes providing in a container, e.g., an electrically insulating container, a liquid composition comprising a binder polymer chains and a solvent. The binder polymer can have a plurality of functional groups, e.g. amine ($NH_2$) groups. An article to be processed, which comprises a polymeric surface, is at least partially submerged in the liquid composition. The container which has the at least partially submerged article is then placed in a plasma reactor chamber. Energy sufficient to generate a gas phase plasma is then applied to a volume of gas above the surface of the liquid composition. A gas-phase plasma generated from the volume of gas and sustained above the surface of the liquid composition causes or accelerates formation of a binder polymer layer on the polymeric surface of the article. For example, the deposition may be caused or accelerated by a chemical a reaction between functional groups (e.g., $NH_2$ groups) of the polymer and atoms, e.g., oxygen atoms, of the polymeric surface may be facilitated. Thereafter, in some embodiments, nanoparticles may be attached to the binder polymer layer. In various embodiments, the gas phase plasma does not come in direct contact with the polymeric surface of the article on which the binder polymer layer is formed. Furthermore, the liquid composition, the article and the container are not electrically connected such that they are electrically floating while the deposition is caused or accelerated.

Plasma-Assisted Nanoparticle Coating Method

Figure 7:
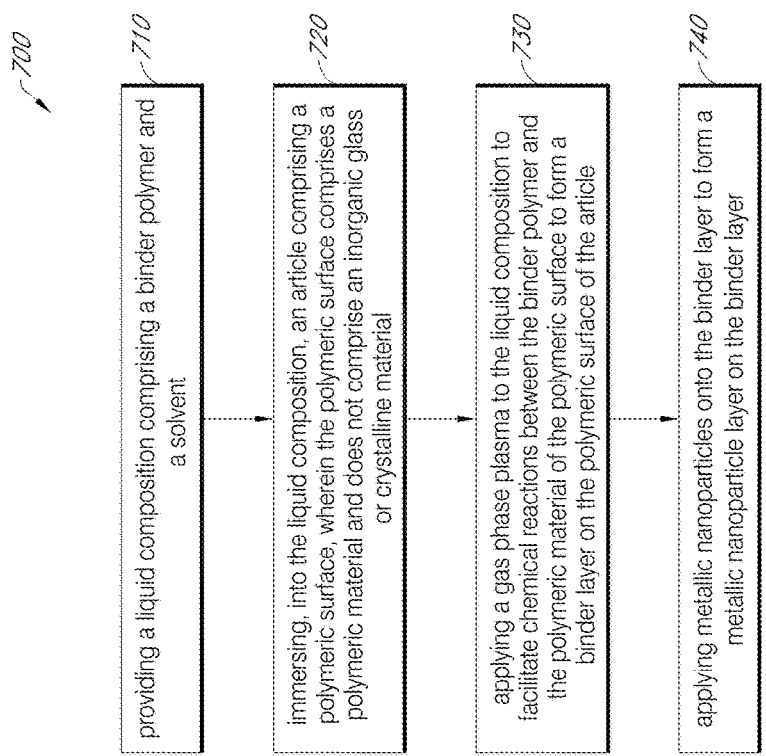
FIG. 7 is a flow chart illustrating a method of coating a polymeric substrate with a layer of metallic nanoparticles for fabricating a polymer-based test vehicle by plasma-treating the polymeric substrate under liquid immersion, according to embodiments.

Referring to FIG. 7, a method 700 of coating a polymeric substrate with a layer of metallic nanoparticles is described, according to various embodiments. The method 700 includes, at a process 710, providing a liquid composition comprising a binder polymer and a solvent. The method 700 additionally includes at a process 720 at least partially immersing, into the liquid composition, an article comprising a polymeric surface. The polymeric surface comprises a polymeric material and does not comprise an inorganic glass or crystalline material. The method 700 additionally includes, at a process 730, applying a gas phase plasma to the liquid composition to facilitate a chemical reactions between the binder polymer and the polymeric surface to form a binder layer on the polymeric surface of the article. The method 700 further includes, after forming the binder layer, at a process 740, applying metallic nanoparticles onto the binder layer to form a metallic nanoparticle layer on the binder layer. In the following with respect to FIGS. 8A-8E, various stages of the process of coating polymeric substrates with a layer of metallic nanoparticles are described in greater detail.

Liquid Composition

Figure 8A:
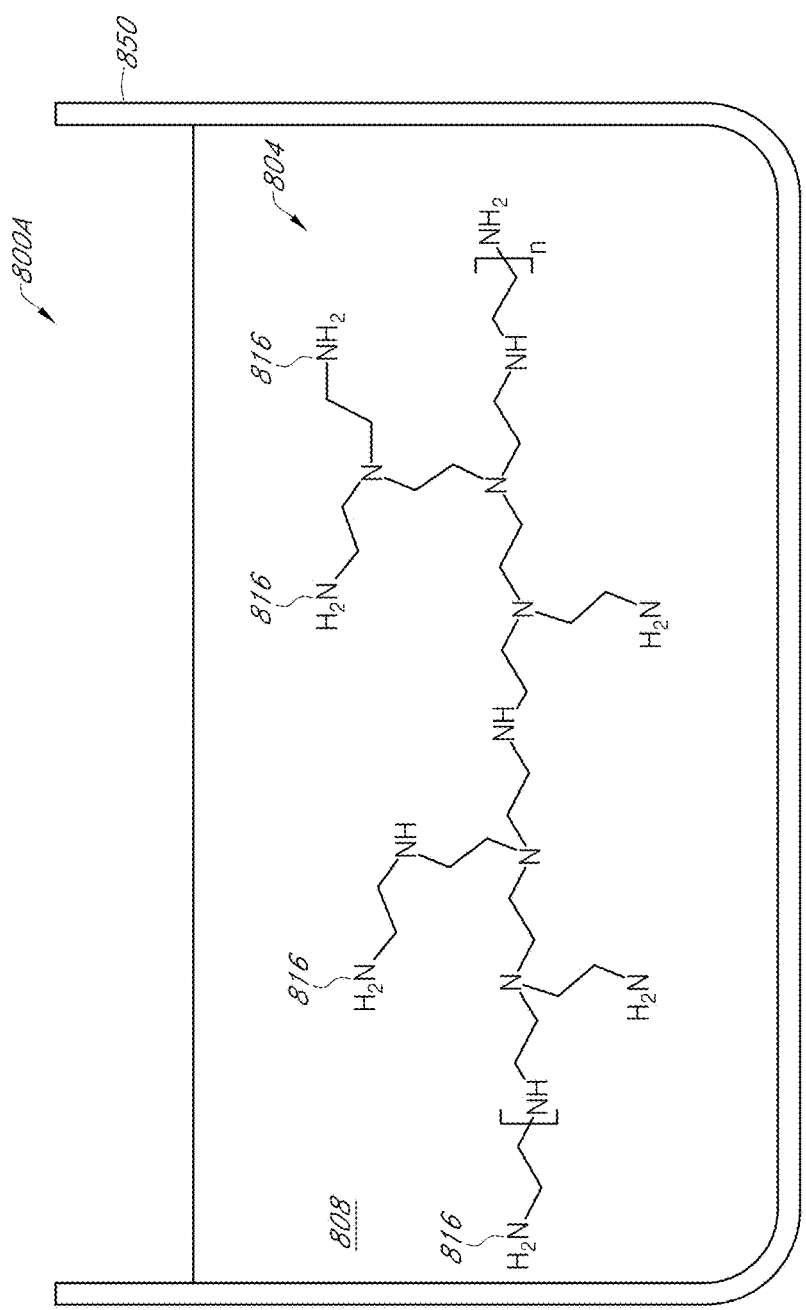
FIGS. 8A-8E illustrate various stages of coating a polymeric substrate with a layer of metallic nanoparticles for fabricating a polymer-based test vehicle by plasma-treating the polymeric substrate under liquid immersion, according to embodiments.

FIG. 8A illustrates providing a liquid composition 800A comprising a binder polymer and a solvent, the binder polymer having a plurality of functional groups, according to embodiments. The liquid composition 800A comprises a mixture or a solution that includes the solvent 808 and the binder polymer 804. The binder polymer 804 may be dissolved in the solvent 808 to form a solution, partially dissolved in the solvent 808 to form a partial solution/partial mixture, or otherwise undissolved in the solvent 808 to form a mixture. In the illustrated embodiment, the liquid composition 800A is prepared in a container 850 that is electrically insulating. For example, the container 850 may be a dielectric container, e.g., an optically transparent dielectric container, such as, e.g., a petri dish. The binder polymer 804 is a polymer-based material which functions to immobilize nanoparticles on a substrate, and more particularly functions to immobilize metallic nanoparticles on a polymeric substrate at a later stage in the process. The binder polymer 804 can immobilize the nanoparticles, for example, by binding to surface atoms of the polymeric substrates at some locations within a chain of the binder polymer 804 while simultaneously binding to metallic particles at some other locations within the chain (described later in more detail). In some embodiments, the binder polymer 804 includes a plurality of binder functional groups 816, which are amine terminals ($NH_2$) in the illustrated embodiment. Other binder functional groups 816 are possible, such as thiols (SH), phosphonic acids (—$PO(OH)_2$ or —$PO(OR)_2$)

In some embodiments, the binder polymer 804 includes a cationic polymer such as poly diallyl dimethyl ammonium, poly diallydimethylammonium chloride, poly allylamine hydrochloride, poly 4-vinylbenzyltrimethyl ammonium chloride, polyamines derived from ethylenamine including diethylenetriamine (DETA), ($H_2N$—$CH_2CH_2$—$NH$—$CH_2CH_2$—$NH_2$, an analog of diethylene glycol), triethylenetetramine (TETA), ($H_2N$—$CH_2CH_2$—$NH$—$CH_2CH_2$—$NH$—$CH_2CH_2$—$NH_2$), tetraethylenepentamine (TEPA), ($H_2N$—$CH_2CH_2$—$NH$—$CH_2CH_2$—$NH$—$CH_2CH_2$—$NH$—$CH_2CH_2$—$NH_2$), pentaethylenehexamine (PEHA) ($H_2N$—$CH_2CH_2$—$NH$—$CH_2CH_2$—$NH$—$CH_2CH_2$—$NH$—$CH_2CH_2$—$NH$—$CH_2CH_2$—$NH_2$), polyethylene amine, hyperbranched polymers including polyamidoamine dendrimers, polypropylimine dendrimers, polyethyleneimine (PEI), or a mixture thereof. In other embodiments, the binder polymer 804 includes an anionic polymer such as poly acrylic acid, poly sodium 4-styrene sulfonate, poly vinylsulfonic acid, poly sodium salt, poly amino acids, or a mixture thereof. In some embodiments, binder polymers include linear or multi-branched polyethyleneimine (PEI), ethylenediamine or other crosslinkable molecules suitable for forming amide bonds on a surface of a polymeric substrate. In the illustrated embodiment of FIG. 8A, for illustrative purposes, the binder polymer 804 is an amine functionalized organic molecules including polymers.

The solvent can include any suitable solvent that can dissolve the binder molecules to form the solution. Suitable solvents include, for example, water, sodium hydroxide, ammonium hydroxide, or a mixture thereof, among other suitable solvents that can dissolve or otherwise hold the binder polymer 804 in the liquid composition 800A as a mixture.

Advantageously, in some embodiments, particular amounts of the binder polymer 804 and the solvent 808 can be mixed in appropriate volume ratios to control the pH level of the liquid composition 800A within a desired range that is optimized, in later processes, for the binding reactions between the binder polymer 804 and the surface atoms of the substrate and between the binder polymer 804 and the nanoparticles. In some embodiments, prior to mixing, the solvent 808 can be prepared to have a pH level between about 5 and 9, between about 6 and 8, for instance 7. After mixing, the combination of the binder polymer and the solvent can be controlled to have a pH between about 8 and 12, between about 9 and 11, for instance about 10. For example, when the binder polymer includes TETA, the volume ratio between water and TETA of 0.01%~10% can be used to optimize the pH.

The inventors have also found that the binder polymer 804 having a particular molecular weight can be advantageous for optimizing the density of binding locations between the chains of the binder polymer and the surface atoms of the substrate and the nanoparticles. The molecular weight of the binder polymer 804 may be chosen to have a range between about 100 daltons and about $1\times10^7$ daltons, between about 1000 daltons and about $1\times10^6$ daltons, or between about 1000 daltons and about $1\times10^5$ daltons, for instance about 10,000 daltons.

Insulating Container

Still referring to FIG. 8A, the liquid composition 800A is provided in a dielectric container 850 that is electrically insulating. The dielectric container 812 can be formed of any suitable insulating material that does not conduct electricity, such as polymeric materials including, e.g., polyethylene terephthalate (PET, polyethyleneterephthalate), polymethyl methacrylate (PMMA, polymethylmethacylate), polystyrene (PS, polystyrene), polycarbonate (PC, polycarbonate), to name a few. In some embodiments, dielectric container 812 comprises an inorganic glass or crystalline material, such as, for example, $SiO_2$ or $Al_2O_3$.

Figure 8B:
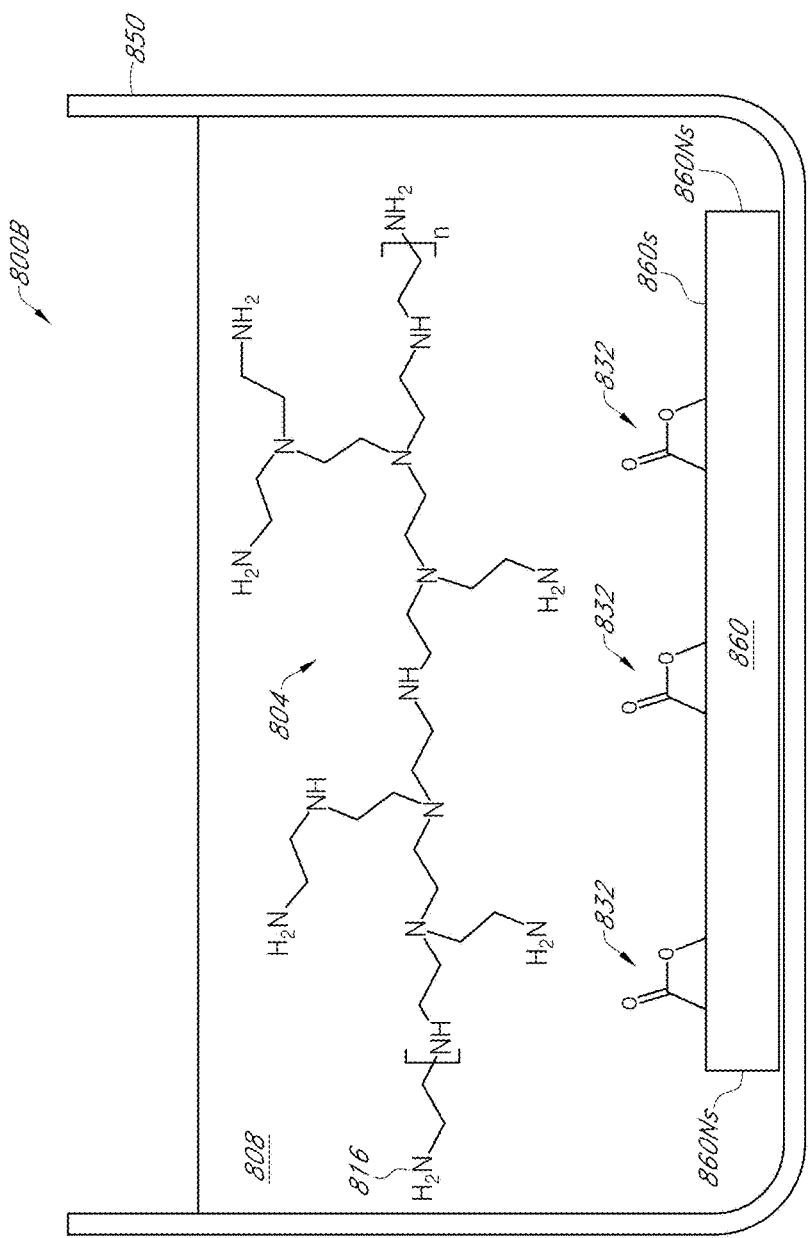
Figure 8C:
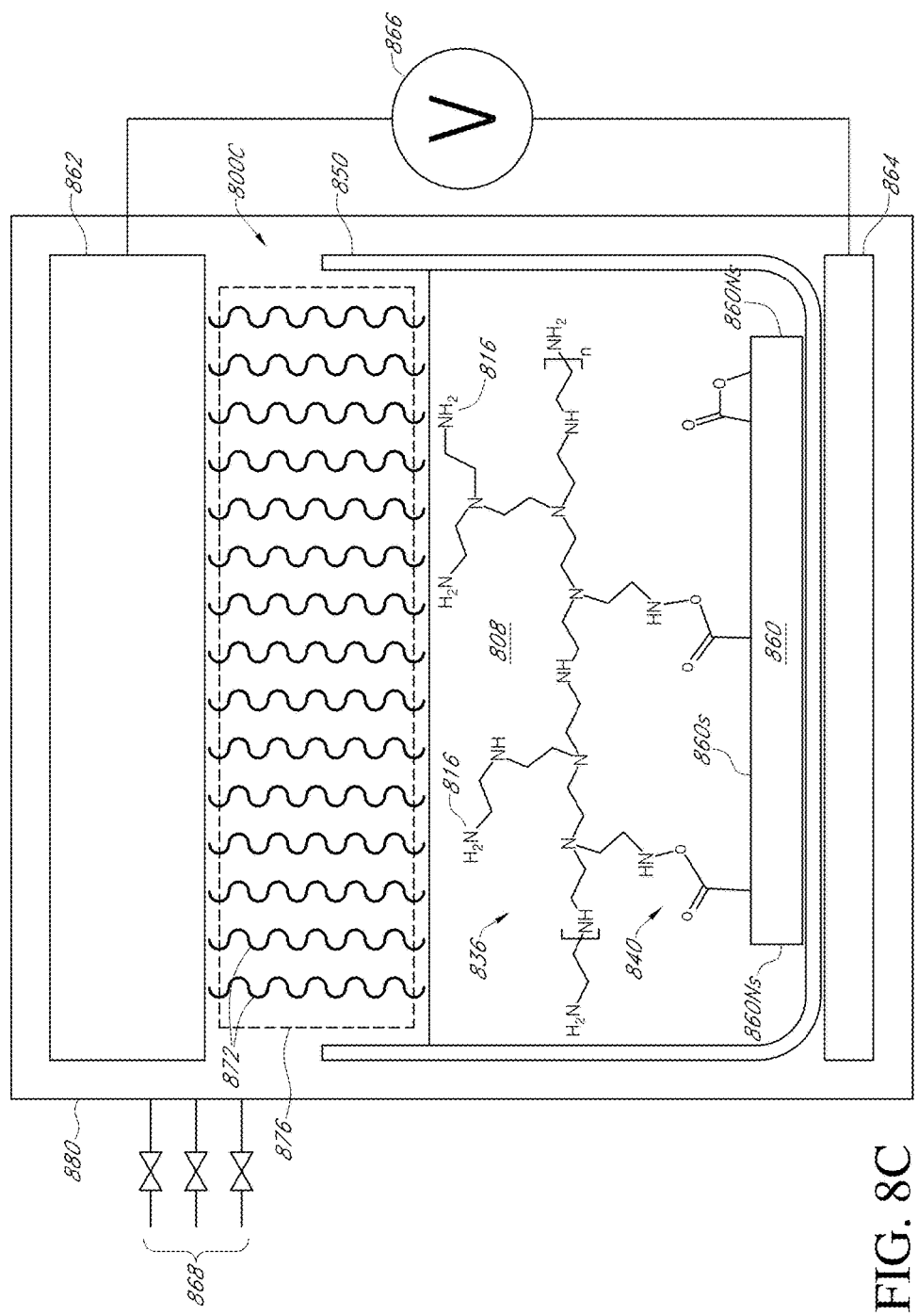

While the liquid composition 800A can be prepared in a non-dielectric container, e.g., a conductive vessel, the liquid composition 800A is transferred to a dielectric container 812 prior to subjecting the liquid composition 800A to plasma, as described in more detail infra with respect to FIG. 8C. Providing the dielectric container 850 comprising an insulating material that does not conduct electricity can provide several advantages. For example, the dielectric container 850 can provide improved protection of the liquid composition 800A and the dielectric container 850 against arcing and/or dielectric breakdown when the dielectric container 850 containing the liquid composition 800A is subjected to plasma conditions (described more in detail with respect to FIG. 8C). That is, when the dielectric container 850 is placed on a substrate holder that can serve as an electrode of a plasma processing chamber, the dielectric container 850 can electrically float the liquid composition and articles that are subsequently placed in the liquid composition 800A.

Submerging Polymeric Surface in the Liquid Composition

FIG. 8B illustrates at least partially immersing or submerging, into the liquid composition 800B, an article, e.g., a polymeric substrate 860, according to embodiments. The polymeric substrate 860 has a polymeric surface 860S, according to embodiments. Portions of the polymeric surfaces 860S exposed to the liquid solution 800B, e.g., immersed in the liquid composition 800B, directly contact the liquid composition 800B. According to embodiments, the polymeric surface 860S has an exposed carbon-based chain, such as, e.g., polyethylene terephthalate (PET, polyethyleneterephthalate), polymethyl methacrylate (PMMA, polymethylmethacylate), polystyrene (PS, polystyrene), polycarbonate (PC, polycarbonate), and cyclic olefin high polymer (COC, cyclic olefin copolymer), to name a few. In some embodiments, the polymeric surface 860S does not comprise an inorganic glass or crystalline material, such as, for example, $SiO_2$ or $Al_2O_3$.

In the illustrated embodiment, the substrate 860 is immersed into the liquid composition 800 comprising a mixture or a solution that includes the solvent 808 and the binder polymer 804, as described above with respect to FIG. 8A. The polymeric surface 860S having thereon a plurality of substrate functional groups 832 come into contact with the binder polymer 804 having binder functional groups 816. The polymeric surface 860S has a plurality of substrate functional groups 832 that are adapted to chemically react with binder functional groups 816. In the illustrated embodiment, the substrate functional groups 832 are carbonate groups (—O—(C═O)—O—). Other functional groups 832 on the polymeric surface 860S are possible, such as isothiocyanate, isocyanate and amine terminals.

In FIG. 8B, for illustrative purposes, the substrate 860 is depicted as being fully immersed in the liquid composition 800 such that an entire surface of the polymeric surface 860S contacts the liquid solution 808. However, it will be appreciated that in other embodiments, some portions of the substrate 860 may be immersed, while other portions remain outside of the liquid composition 800B. It will be appreciated that the portions that come in contact with the liquid composition 808 react with the binder polymer 804 and become subsequently coated with nanoparticles, while other portions that do not come in contact with the liquid composition 808 do not react with the binder polymer 804 and do not get coated with nanoparticles, as described infra.

It will further be appreciate that, in other embodiments, the substrate 860 may have a non-active surface 860NS. In these embodiments, a non-active surface 860NS can be a surface of the substrate 860 where metallic nanoparticles may not be desired, such that metallic nanoparticles can be selectively formed only on the polymeric surface 860S, as described infra with respect to FIG. 8E. For illustrative purposes only, the non-active surface 860NS is formed on a side surface of the substrate 860. However, it will be appreciated that the non-active surface 860NS can be formed anywhere on the surfaces of the substrate 860. For example, the non-active surface 860NS and the polymeric surface 860 can both be formed on the upper surface of the substrate 860. The non-active surfaces 860NS can be formed of a different material compared to the polymeric surface 860S, formed of the same material as the polymeric surface 860S but functionalized with a functional group different from the substrate functional groups 832 or unfunctionalized or otherwise inactivated such that a reaction with the functional groups 816 of the binder polymer 804 is prevented in a subsequent processes (FIG. 8C).

Plasma Reactor for Gas Phase Plasma Processing Under Solution Immersion

FIG. 8C illustrates, after submerging at least a portion of the polymeric substrate 860 into the liquid composition, applying a gas phase plasma to the liquid composition to cause a chemical reaction between the binder functional groups of the binder polymer and the substrate functional groups of the polymeric surface, thereby forming a binder layer on the polymeric surface 860S, according to embodiments. The container 850 is placed inside a plasma reactor 880.

The plasma reactor 880 is configured for gas-phase plasma processing of an article under solution immersion, according to embodiments. The plasma reactor 880 comprises at least one electrode that can be energized to impart energy to gas phase atoms or molecules above the surface of the solvent to initiate plasma generation. In the illustrated embodiment, the reactor 880 comprises a top electrode 862 and a bottom electrode 864, and is configured to receive the container 850. The reactor 880 is configured to receive, through one or more of gas inlets 868 connected the reactor 880, at least one gas species for generating a gas phase plasma. The reactor can also be connected to a vacuum pump (not shown) to control the pressure inside the reactor. In particular, the reactor is configured to control the pressure inside the reactor and to maintain suitable partial pressures of all components of the liquid composition 800C, including the solvent 808 and the binder polymer 836 such that the components do not completely evaporate during the gas-phase plasma processing. For example, the reactor is configured to generate and maintain the plasma under subatmospheric and atmospheric conditions, e.g., by controlling and maintaining a pressure between about 1 mtorr and about 780 torr, between about 1 torr and about 760 torr, or between about 100 torr and about 760 torr.

After receiving the at least one gas species through the at least one valve 868, energy 872 is applied to the volume of gas between the surface of the liquid composition 800C and the top electrode 862 through at least one of the top electrode 862 and the bottom electrode 864, thereby generating a plasma 872 between the surface of the liquid composition 800C and the top electrode 862. It will be appreciated that while the top and bottom electrodes 862 and 864 are depicted as being disposed inside the reactor 880, one or both of the top and/or bottom electrodes 862 and 864 can be placed outside of the reactor 880.

As defined herein, an electrode of a plasma reactor is an element through which energy can be imparted to a volume of gas and can include, for example, a plate of a capacitor, a coil of an inductor and the like. Without loss of generality, in one embodiment, the plasma reactor is a DC or an AC plasma reactor in which a DC power or an AC power is applied between the first and second electrodes 862 and 864 to form a capacitively coupled plasma discharge. In some embodiments in which the plasma reactor is a DC plasma reactor, the plasma reactor is configured as a pulsed DC plasma reactor in which the DC power can be applied in a pulsed form. A pulsed DC voltage can be bipolar or unipolar. When bipolar, the DC voltage can be symmetric or asymmetric in amplitudes in opposite polarities. The DC or AC power can be applied through one or both of the first and second electrodes 862 and 864, and can be driven by a power supply 866. While in the illustrated embodiment both first and second electrodes 862 and 864 are connected to the power supply 866, it will be appreciated that in other embodiments, only one of the two electrodes can be "hot" while the other is electrically grounded or floated. In addition, when one of the two electrodes are "hot" and receives pulsed DC or AC power, the other electrode can be placed under a bias, e.g., a DC bias such that charged species can accelerate towards the liquid composition 800C.

Other types of plasma generation can be employed. For example, the plasma reactor 880 can be an inductively coupled plasma (ICP) reactor or an electron cyclotron resonance (ECR) plasma reactor in which the energy is supplied by electrical currents produced by time-varying magnetic fields which can enhance the densities of the plasmas under some circumstances.

Gas Phase Plasma Processing to Form a Polymer Layer Under Solution Immersion

Still referring to FIG. 8C, energy 872 is applied to the volume of gas between the surface of the liquid composition 800C and the top electrode 862 through at least one of the top and bottom electrodes 862 and 864 to generate a gas phase plasma 872.

In the illustrated embodiment, the substrate 860 is entirely submerged in the liquid composition 800C such that the liquid composition 800C separates the polymeric surface 860S and the plasma 872. That is, the polymeric surface 860S onto which the binder polymer 836 is attached is not directly exposed to the plasma 872.

In the illustrated embodiment, the entire substrate 860 is submerged such that the entire polymeric surface 860S is submerged under the liquid composition 800C. However, in other embodiments, the substrate 860 is only partially submerged such that only a portion of the surface 860 is submerged under the liquid composition 800C.

In some embodiments, prior to generating the plasma 872, the composition of the gas in the plasma reactor 880 is adjusted by introducing one or more gases into the plasma reactor 880 through one or more gas inlets 868. In some embodiments, the volume of gas can include an inert gas such as He, Ar, Ne and Xe, or mixtures thereof. In some embodiments, the volume of gas can include one or more gases selected from $O_2$, $O_3$, $N_2$, $H_2$, $NH_3$, $N_2O$, and NO, and mixtures thereof, among other gases. It will be appreciated, however, that a separate nitrogen containing gas such as $N_2$ or $NH_3$ is not needed to cause a chemical reaction between the substrate functional groups and the binder functional groups containing nitrogen because the nitrogen atoms are provided by the binder functional groups themselves (e.g., $NH_2$).

Still referring to FIG. 8C, the plasma 872 is generated above a surface of the liquid composition 860C, for example directly above the liquid composition 860C. In the illustrated embodiment, the plasma 872 is generated between the first electrode 860 and the surface of the liquid composition 860C by imparting energy to the volume of gas disposed therebetween using one of the power delivery methods described above. For example, in some embodiments, one or both of the electrodes 860 and/or 862 can be driven under AC or pulsed DC conditions at a frequency between about 10 KHz and about 1 MHz, for instance a regulated frequency of 100 KHz. In other embodiments, the frequency can be higher, for example a regulated RF frequency of 13.56 MHz, or a regulated microwave frequency of 2.45 GHz. A peak-to-peak amplitude of applied bias can be, for example, between about 100 V and about 100 kV, or between about 1 kV and 10 kV.

Various optical and chemical processes of the glow discharge of the plasma 872 can contribute to the reaction between the binder functional groups and the substrate functional groups. For example, without being bound to any theory, the reactions can at least partly be facilitated by diffusion of various species, e.g., radicals, into the liquid composition 800C from the plasma. In addition, without being bound to any theory, the reactions can also be facilitated by various atomic transitions between states (e.g., excited and ground states) of the species of the plasma 872 and/or dissociation and recombination reactions between various neutral and charged species within the plasma 872, which can cause emission of photons in the visible and in the UV. Thus, without being bound to such theories, the plasma species and photons generated from the sustained plasma 872 causes a chemical reaction between the binder functional groups 816, e.g., NH$_2$, of the binder polymer 836, and surface functional groups of at least the portion of the polymeric surface 860S, e.g., oxygen atoms of a carbonate group (—O—(C═O)—O—), such that a layer of the polymer binder 836 is formed on the polymeric surface 860S, as in the illustrated embodiment of FIG. 8C.

Other embodiments are possible, where the plasma does not sustain a glow discharge. Yet other embodiments are possible, where the plasma is generated outside of the chamber space above the surface of the liquid composition 860C and is subsequently transferred to the space above the surface of the liquid composition 860C.

The inventors have found that the chemical reaction is caused when the plasma 872 is sustained above the liquid composition 800C for a plasma treatment duration between about 1 msec and about 1 hour, between about 1 sec and about 1 hour, between about 1 sec and about 10 min, or between about 1 sec and about 5 min. The pressure of the reactor 880 during the duration is placed under an average pressure between about 1 and about 760 torr, and can be maintained in steady state by either constant flow of gases or by a pressure servo mechanism.

As described above with respect to FIG. 8A, the container 850 is an electrically insulating container, e.g., a dielectric container. Therefore, in the illustrated embodiment, the substrate 860 and the liquid composition 800C do not directly contact the bottom electrode 864. In addition, there is no other external direct electrical connection that is made to the substrate 860 no to the liquid composition 800C such that, in the illustrated embodiment, the substrate 860 is electrically floated. However, in other embodiments, the substrate 860 can be grounded or placed under an independent bias, e.g., DC bias. It will be appreciated that, however, even when the substrate 860 is electrically floated, the bottom electrode 864 can be independently biased, e.g., DC-biased, to alter, e.g., accelerate charged species within the plasma 872 towards the liquid composition 800C.

The combination of various plasma conditions described above results in facilitation of chemical reactions between the binder polymer 804 (FIG. 8B) and polymeric surface 860S to form a binder layer 836 on the polymeric surface 860S. The binder layer 836 is chemically bound to the polymeric surface 860S through reacted functional groups 840 resulting from a chemical reaction between binder functional groups 816 and substrate functional groups 832. In the illustrated embodiment, the NH$_2$ groups of the binder polymer 804 (FIG. 8B) reacts with oxygen atoms of carbonate groups (—O—(C═O)—O—) of the polymeric surface 860S to form the binder layer 836.

Preparation of a Nanoparticle Solution

Figure 8D:
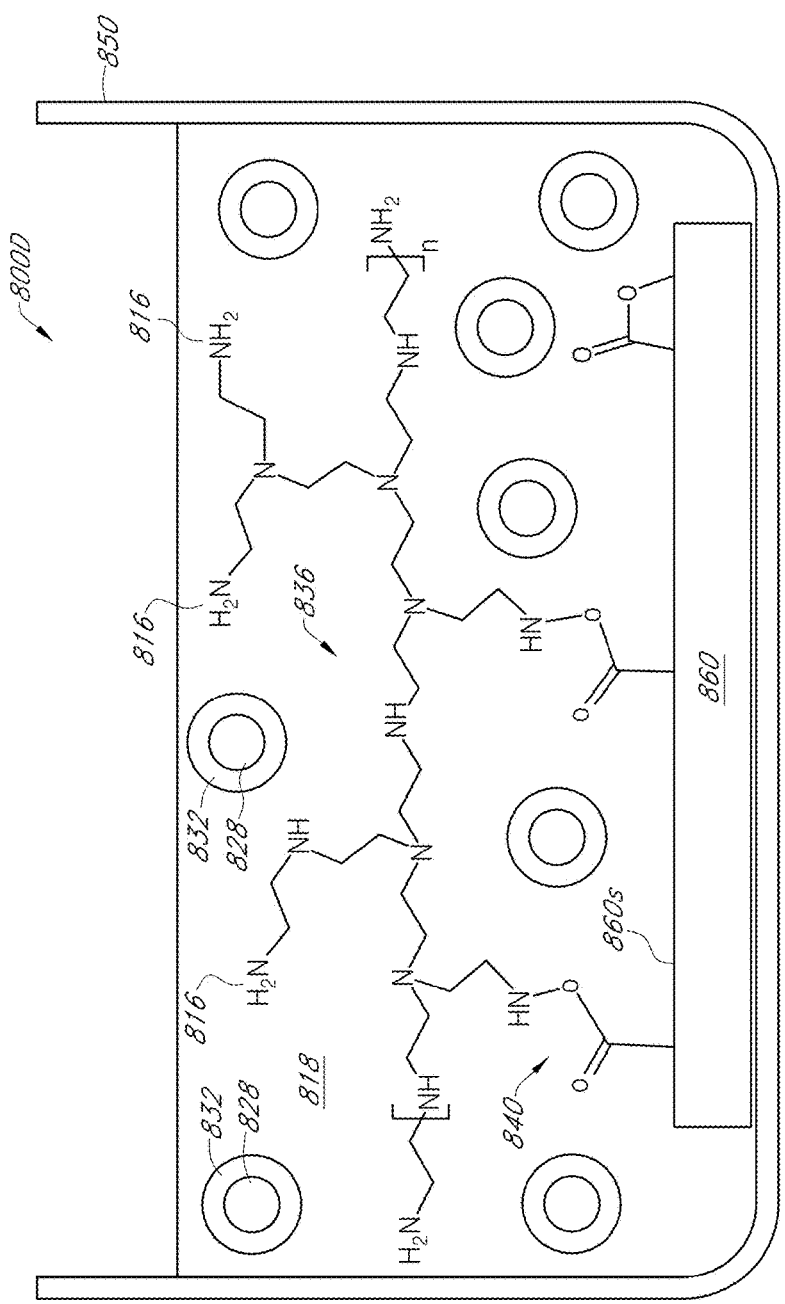

Referring to FIG. 8D, after causing the chemical reaction between binder functional groups and substrate functional groups to form the binder layer 836 chemically attached to the polymeric surface 860S, the liquid solution 800C (FIG. 8C) containing unreacted binder polymer may be discarded from the container, and the substrate 860 may be washed. Subsequently, the substrate 860 may be submerged in a nanoparticle solution 800D comprising a nanoparticle solvent 818 and a plurality of metallic nanoparticles 828.

The nanoparticle solution 800D can be a suitable solvent, e.g., an aqueous solution, e.g., distilled water. The metallic nanoparticles 828 can comprise one of suitable metallic materials having morphologies described above with respect to FIGS. 2A and 2B and are stabilized with a surfactant 832 which can prevent the nanoparticles 828 from coagulating. The surfactant 832 can be a suitable compound selected from sodium citrate, ascorbic acid, 4-mercaptobenzoic acid, meso-2,3-dimercaptosuccinic acid, mercaptosuccinic acid, succinic acid, sodium dodecylsulfate, sodium octylsulfate, sodium decanesulfonate, lysine, glucose, cetyltrimethyl ammonium bromide (CTAB), hexadecyltrimethylammonium bromide, tetradecylammonium bromide, tetraoctylammonium bromide, tetrahexylammonium bromide, dodecyltrimethylammonium bromide, and cetylpyridinium chloride, to name a few.

In the nanoparticle solution 800D, the nanoparticles 828 can have a median size selected to be between about 1 nm and about 10 nm, for instance about 5 nm; between about 5 nm and about 20 nm, for instance about 10 nm; between about 10 nm and about 30 nm, for instance about 20 nm; between about 20 nm and about 40 nm, for instance about 30 nm; between about 30 nm and about 50 nm, for instance about 40 nm; between about 40 nm and about 60 nm, for instance about 50 nm; between about 50 nm and about 80 nm, for instance about 60 nm; between about 60 nm and about 100 nm, for instance about 80 nm; between about 80 nm and about 150 nm, for instance about 100 nm; between about 100 nm and about 200 nm, for instance about 150 nm; between about 150 nm and about 250 nm, for instance about 200 nm; between about 200 nm and about 300 nm, for instance about 250 nm; between about 250 nm and about 400 nm, for instance about 300 nm; between about 300 nm and about 700 nm, for instance about 500 nm; between about 500 nm and about 900 nm, for instance about 700 nm; or between about 700 nm and about 1100 nm, for instance about 900 nm. The median size can be, e.g., a minimum lateral dimension of the nanoparticle 828 measured along one of directions of symmetries of the nanoparticle 828.

In some embodiments, the median size of the nanoparticles 828 have a relatively narrow standard deviation between, e.g., about 0.1% and about 2%, about 2% and about 4%, about 4% and about 6%, about 6% and about 8%, about 8% and about 10%.

It will be appreciated that a particular median size of the nanoparticles 828 can be selected such that the resulting peak wavelength of the LSPR is between a particular desired wavelength range. In various embodiments, the median size can be selected such that the peak of the LSPR is between about 515 nm and about 525 nm, for instance 520 nm; between about 525 nm and about 535 nm, for instance 530 nm; between about 535 nm and about 545 nm, for instance 540 nm; between about 545 nm and about 555 nm, for instance 550 nm; between about 555 nm and about 565 nm, for instance 560 nm; between about 565 nm and about 575 nm, for instance 570 nm; or between about 575 nm and about 585 nm, for instance 580 nm.

It will be appreciated that the particle sizes can be selected to have a specific LSPR peak absorbance wavelength, and the standard deviation of the particle sizes can be tailored to have a specific width of the LSPR spectrum described above with respect to FIGS. 4A and 4B, e.g., less than 100 nm, or less than 80 nm.

Attaching Metallic Nanoparticles to the Binder Polymer

Figure 8E:
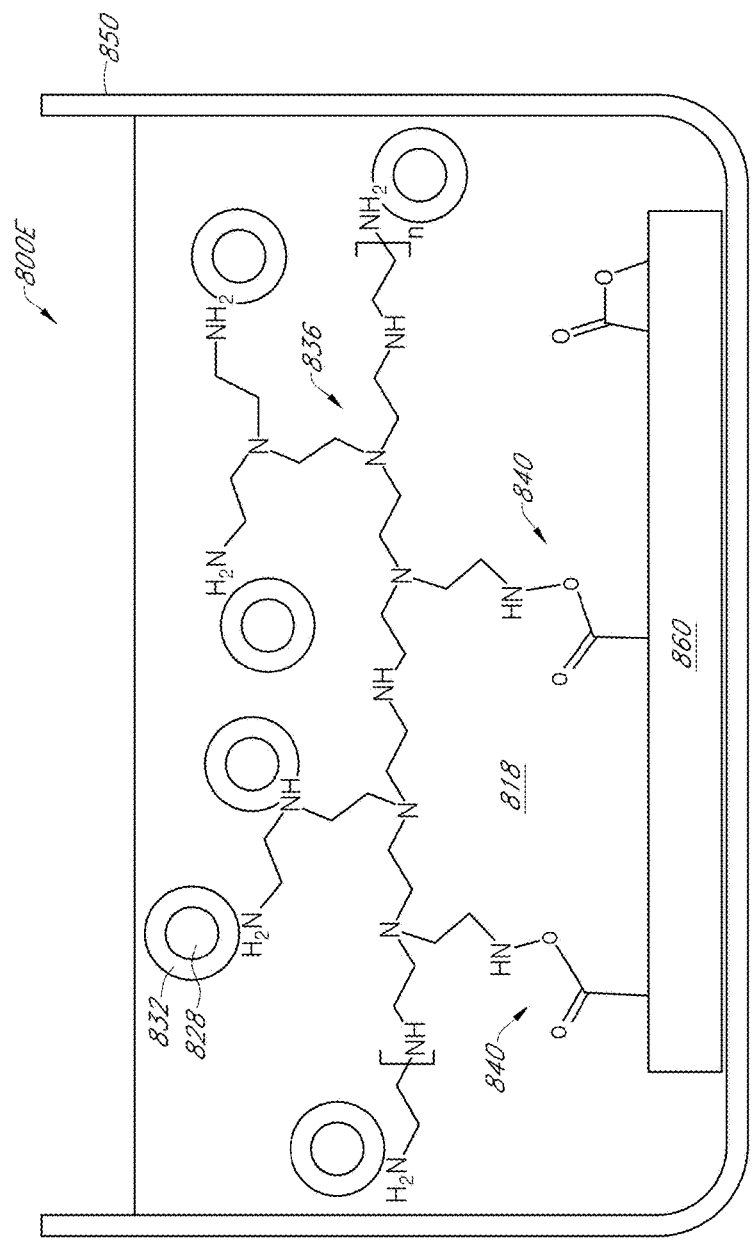

Referring to FIG. 8E, after submerging substrate 860 in the nanoparticle solution 800D comprising the nanoparticle solvent 818 and the metallic nanoparticles 828, the nanoparticles 828 are attached to unreacted or remaining ones of the binder functional groups 816. According to embodiments, a chemical reaction occurs between unreacted or remaining ones of the binder functional groups 816, e.g., NH$_2$, that are present after attaching the binder polymer 836 to the polymeric surface 860S as described above with respect to FIG. 8D, thereby forming a layer of metallic nanoparticles on the polymeric surface 860S. While in the illustrated embodiment, the binder functional groups 816 that attach to the substrate functional groups 832 (FIG. 8B) are the same as the binder functional groups 816 that attach to the nanoparticles 828, other embodiments are possible, where the binder functional groups are different and selectively attach to one but not the other of the substrate functional groups 832 or the nanoparticles 828.

As formed, the layer of nanoparticles can have any of the size range, standard deviation and a peak wavelength described above with respect to FIG. 8D. In addition, the layer of metallic nanoparticle has a surface density that can be optimized for LSPR based at least in part on the surface density and inter-nanoparticle distance of the nanoparticles. In one example, for nanoparticles having a size range between about 1 nm and about 50 nm, the surface density can be between about $1 \times 10^8/cm^2$ and about $1 \times 10^{13}/cm^2$, between about $5 \times 10^8/cm^2$ and about $5 \times 10^{12}/cm^2$ or between about $1 \times 10^9/cm^2$ and about $2 \times 10^{12}/cm^2$.

In addition, the nanoparticles can have a median inter-nanoparticle distance that is between 1 nm and about 10 nm, between 10 nm and about 100 nm, between 100 nm and about 1000 nm, between 1000 nm and about 10,000 nm or between 10,000 nm and about 100,000 nm. In addition, the nanoparticles can have a median inter-nanoparticle distance standard deviation between about 0.1% and about 2%, between about 2% and about 4%, between about 4% and about 6%, or between about between about 6% and about 8%.

Substrate Surface Orientations

Figure 8F:
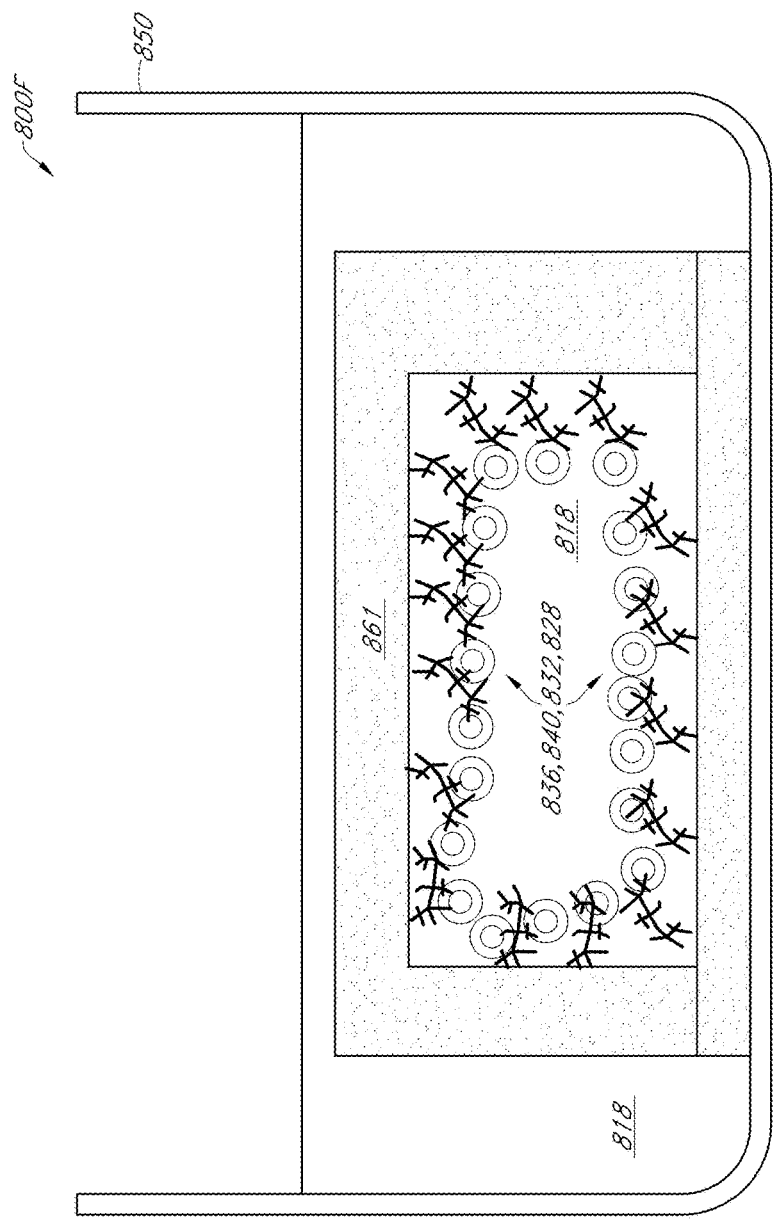
FIG. 8F illustrates a polymer-based test vehicle having a surface that does not face the plasma that is processed according to processes described in FIGS. 8A-8E, according to embodiments

In FIG. 8C, for illustrative purposes only, the plasma 872 is generated above a surface of the liquid composition 800C, thereby causing or accelerating formation of the layer of binder polymer 836 on the polymeric surface 860S which faces the plasma 872. However, other embodiments are possible, where the polymeric surface on which the polymer layer is formed does not face the plasma 872, or at least partially faces away from the plasma, such may be the case when the substrate 860 includes a surface which has a curvature, a flection, an arc, a bend, a bow, a twist, a loop, a turn, or the like. As one illustrative example, in FIG. 8F, the polymeric transparent substrate 861 has a cavity having inside (upper, lower, and side) surfaces. The substrate 861 may have openings such that the cavity is filled with the solvent 818/the liquid composition 800F. Similar to the substrate 860 of FIG. 8C, when submerged under the solvent 818/the liquid composition 800F, the inside surfaces of the cavity of the substrate 861 do not come in contact with the plasma (not shown, similar to FIG. 8C) and are separated from the plasma by the solvent 818/the liquid composition 800F. In addition, the inside surfaces are further separated from the plasma by the upper portion of the substrate 861 itself, in addition to being separated by the solvent 818/the liquid composition 800F. The lower surface inside the cavity faces the plasma, the upper surface inside the cavity faces away from the plasma, and the side surfaces inside the cavity are oriented at an angle, e.g., 900, from the horizontal surface of the solvent 818/the liquid composition 800F. Advantageously, when processed under process conditions similar to the conditions described above with respect to FIGS. 8A-8E, upper, lower, and side surfaces have binder polymer 836 layers that have substantially uniform thicknesses, where on average, the thicknesses of the layers of the binder polymer 836 on different surfaces are within about 10% of each other or within about 5% of each other. In addition, differences in the surface densities of the nanoparticles on upper, lower, and side surfaces can be less than about 10%, or less than about 5%.

Auto-Calibrating LSPR Measurement System and Method

When making LSPR measurements on a sample described above with respect to FIGS. 2A and 2B, quantitative information with respect to the amount of target molecules attached to a polymeric substrate is often needed. However, quantitative determination of the amount of target molecules are often hampered because the signal from LSPR measurements can vary significantly due to varying external conditions such as, for example, temperature. In the following, an auto-calibrating LSPR measurement system and associated measurement methods are described, in which references that vary with the changing environment by the similar amount as the sample are advantageously employed, such that any fluctuation in the LSPR signal is auto-calibrated each time an LSPR measurement is made.

Self-Calibrating LSPR Measurement System

Figure 9:
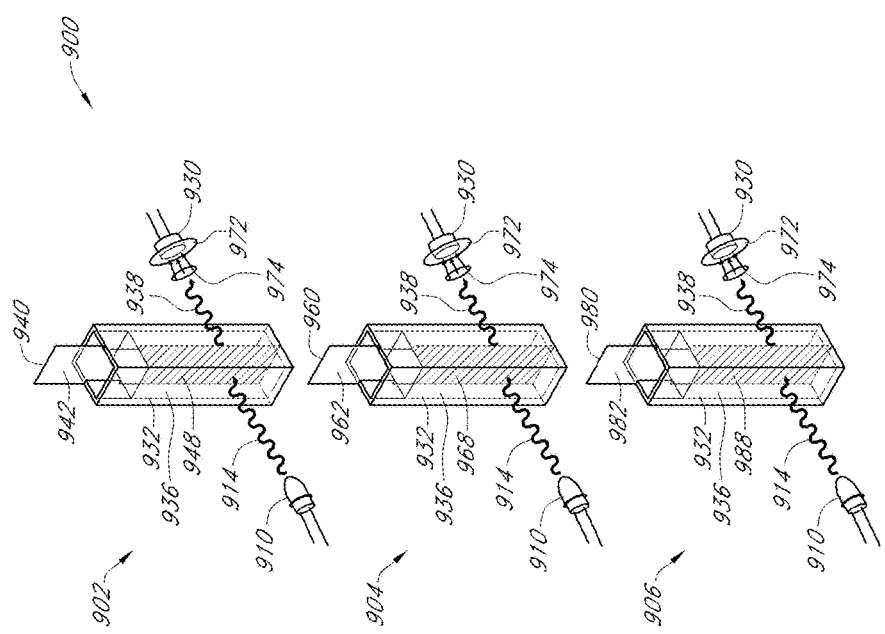
FIG. 9 illustrates an auto-calibrating LSPR method of quantitatively determining the amount of a target molecule attached to a polymer-based test vehicle using control vehicles having known concentrations of target molecules, according to embodiments.

FIG. 9 illustrates an auto-calibrating localized surface plasmon resonance (LSPR) measurement system 900 for detecting target molecules that may be attached to a surface of a test vehicle, according to embodiments. The auto-calibrating LSPR system 900 includes a first reference test vehicle 902, a sample measurement test vehicle 904, and a second reference test vehicle 906. Similar to LSPR measurement systems and methods described above with respect to FIGS. 3E and 3F and FIGS. 6B-6D, the auto-calibrating LSPR system 900 includes a plurality of light sources 910 configured to illuminate each of the vehicles 902, 904 and 906 with an incident light 914 and a plurality of photodetectors 930 configured to detect the light 938 transmitted through each of the vehicles 902, 904 and 906.

Each of the vehicles 902, 904 and 906 have respective substrates 940, 960 and 980 that have a first reference coated analysis region 948, a sample coated analysis region 968 and a second reference coated analysis region 988. Each of the vehicles 902, 904 and 906 may also have non-coated portions 942, 962 and 982. Each of the analysis regions 948, 968 and 988 has a respective analysis region surface that comprises a transparent polymeric material described above. At least portions of the surfaces of the coated analysis regions 948, 968 and 988 have a layer of metallic nanoparticles (not shown for clarity) formed thereon, using methods described above with respect to FIGS. 8A-8F. In addition, each of the vehicles 902, 904 and 906 are configured to be placed in a container 932 that is configured to hold and submerge at least the coated analysis regions 948, 968 and 988 of the respective substrates 940, 960 and 980 in a liquid solution 936 that contain target molecules to be detected.

The sample coated analysis region 968 of the sample measurement test vehicle 904 has capturing molecules (not shown for clarity) formed on at least some of the nanoparticles on the sample coated analysis region 968 such that the target molecules that are in the liquid solution 936 can be captured by the capturing molecules, similar to as described above with respect to FIGS. 3E and 3F and FIGS. 6B-6D. Unlike the coated analysis region 968, the first and second coated reference analysis regions 948 and 988 are not configured to capture the target molecules. Instead, the first and second coated references analysis regions 948 and 988 have first and second concentrations of reference molecules attached to the nanoparticles.

In some embodiments, all coated analysis regions 942, 962 and 982 have the same or similar nominal type and concentration of nanoparticles, which can be of a material, a shape and a concentration described above with respect to FIG. 8E. In other embodiments, each of the coated analysis regions 942, 962 and 982 have different nominal type and/or concentration of nanoparticles.

The first reference coated analysis region 948 has a first predetermined concentration of reference molecules attached to the nanoparticles thereon such that a first reference refractive index measured therefrom is different, e.g., a lower, compared to that measured from the sample coated analysis region 968. The second reference coated analysis region 988 has a second predetermined concentration of reference molecules attached to the nanoparticles thereon such that a second reference refractive index measured therefrom is different, e.g., a higher, compared to that measured from the sample coated analysis region 968. In some embodiments, the reference molecules attached to the first and second reference coated analysis region 948 and 988 include the same reference molecules. However, in other embodiments, the reference molecules attached to the first and second reference coated analysis regions 948 and 988 can be different reference molecules. In addition, reference molecules attached to either or both of the first and second analysis regions 948 and 988 can include the same or different molecules compared to the target molecules. However, regardless of the type of molecules attached to the coated analysis regions 942, 962 and 982, while all three coated analysis regions are configured to come in contact with the solution 936 that may contain the target molecules, only the sample coated analysis region 962 is configured to capture the target molecules, while the first and second reference coated analysis regions 942 and 982 have predetermined concentrations of reference molecules that are already formed thereon and are not configured to further capture the target molecules.

It will be appreciated that while the test vehicles 902, 904 and 906 are configured as transmissive LSPR measurement systems similar to those described with respect to FIGS. 3E and 3F, each of test vehicles 902, 904 and 906 can be configured as any one of attenuated total internal reflection (ATR) LSPR measurement test vehicles described above with respect to FIGS. 6A-6D. In these embodiments, each of the test vehicles 902, 904 and 906 is configured such that the light transmitted through the light guiding structures (similar to the light guiding structures 660a-660c of FIGS. 6B-6D) is guided between a first end and a second end under the attenuated total internal reflection (ATR) condition as described above. That is, because the second refractive index $n_2$ of the solution 936 is lower than the first refractive index $n_1$ of the coated analysis regions 942, 962 and 982, a light beam traveling through the light guiding structures is totally internally reflected back into the interior of the light guiding structures.

LSPR Self-Calibrating Measurement Method

Figure 10:
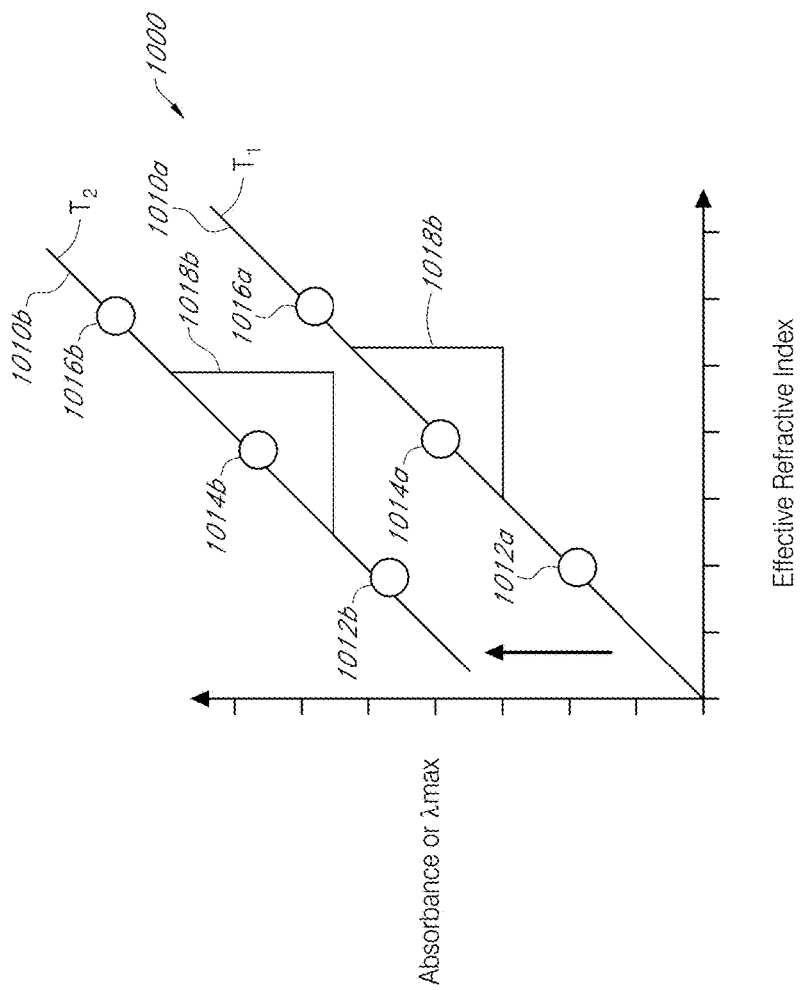
FIG. 10 illustrates an auto-calibrating LSPR method of quantitatively determining the amount of a target molecule attached to a polymer-based test vehicle under temperature-varying conditions by using control vehicles having known concentrations of target molecules, according to embodiments.

Referring to FIG. 10, based on the measured effective refractive indices and absorbance or peak wavelength values from each of the coated analysis regions 942, 962 and 982, the concentration of target molecules attached to the sample coated analysis region 962 can be determined. FIG. 10 shows a graph 1000 illustrating a method of quantitatively determining the amount of a target molecule attached to a polymer-based test vehicle under temperature-varying conditions by using control vehicles having known concentrations of target molecules, according to embodiments. The x-axis represents the effective refractive index ($n_{eff}$) and the y-axis represents the absorbance or peak absorbance wavelength ($\lambda_{max}$). The curves 1010a and 1010b represent absorbance or $\lambda_{max}$ curve v. effective refractive index curves measured at two different temperatures, first temperature $T_1$ and second temperature $T_2 > T_1$, respectively.

The first curve 1010a measured at $T_1$ illustrates a first reference low temperature absorbance 1012a, a sample low temperature absorbance 1014a and a second reference low temperature absorbance 1016a, corresponding to measured refractive indices of test vehicles 902, 904 and 906 described above with respect to FIG. 9 and having the first reference coated analysis region 948, the sample coated analysis region 968 and the second reference coated analysis region 988, respectively. As described above with respect to FIG. 9, the first reference coated analysis region 948 and the second reference coated analysis region 988 have predetermined concentrations of reference molecules that are lower and higher than the concentration of target molecules of the sample coated analysis region 968, respectively.

Inventors have found that the concentration of the target molecules depend linearly on the refractive index regardless of whether the reference molecules are the same or different than the target molecules. Thus, based on the measured refractive index value of the sample coated analysis region 968, a quantitative determination of the target molecules attached to the sample coated analysis region 968 can be determined.

Inventors have also found that the measured absorbance and/or $\lambda_{max}$ is higher for at a given refractive index value when measured at higher temperatures. Furthermore, the inventors have found that the amount of upward shift of the absorbance and/or $\lambda_{max}$ does not depend on the concentration of the target or reference molecules. That is, the slopes 1018b and 1018b between the first and second curves 1010a and 1010b are approximately the same. Thus, the second curve 1010b measured at $T_2$ illustrates a first reference high temperature absorbance 1012b, a sample high temperature absorbance 1014b and a second reference high temperature absorbance 1016b, that are shifted by the same value of absorbance and/or $\lambda_{max}$ compared to the first reference low temperature absorbance 1012b, the sample low temperature absorbance 1014b and the second reference low temperature absorbance 1016b, respectively. Thus, a quantitative measurement of the concentration of the target molecules can be accurately determined from the sample coated analysis region 968 at different temperatures without independently determining the concentration of the reference concentrations of the reference coated analysis regions 948 and 988 at the different temperatures.

Although this invention has been described in terms of certain embodiments, other embodiments that are apparent to those of ordinary skill in the art, including embodiments that do not provide all of the features and advantages set forth herein, are also within the scope of this invention. Moreover, the various embodiments described above can be combined to provide further embodiments. In addition, certain features shown in the context of one embodiment can be incorporated into other embodiments as well. Accordingly, the scope of the present invention is defined only by reference to the appended claims.

What is claimed is:

1. A method of making a polymeric layer on a polymeric substrate, the method comprising:
    providing a liquid composition comprising a binder polymer and a solvent, the binder polymer comprising amine terminals;

providing an article comprising a polymeric surface with one or more functional groups reactive with amine, wherein the polymeric surface does not comprise inorganic glass or crystalline material;

causing the liquid composition to contact the polymeric surface;

applying a gas phase plasma at atmospheric pressure for a period between 1 millisecond and 1 minute to the liquid composition contacting the polymeric surface such that the liquid composition is interposed between the gas phase plasma and the polymeric surface, which to form a polymeric layer comprising cross-linked binder polymers bonded to the polymeric surface by chemical reactions between amine terminals of the binder polymer and the one or more functional groups of the polymeric surface, wherein the gas phase plasma does not comprise ammonia, wherein causing the liquid composition to contact the plasma surface comprises immersing the article into the liquid composition such that the polymeric surface is submerged under the liquid composition when applying the gas phase plasma, and wherein applying the gas phase plasma comprises generating the gas phase plasma using a plasma generator having at least one electrode, wherein while applying the gas phase plasma, none of the at least one electrode of the plasma generator electrically contacts the liquid composition.

2. The method of claim 1, wherein the binder polymer comprises one or more selected from a group consisting of: poly diallyl dimethyl ammonium, poly diallydimethylammonium chloride, poly allylamine hydrochloride, poly 4-vinylbenzyltrimethyl ammonium chloride, polyamines derived from ethylenamine including diethylenetriamine (DETA), $H_2N—CH_2CH_2—NH—CH_2CH_2—NH_2$, an analog of diethylene glycol, triethylenetetramine (TETA), $H_2N—CH_2CH_2—NH—CH_2CH_2—NH—CH_2CH_2—NH_2$, tetraethylenepentamine (TEPA), $H_2N—CH_2CH_2—NH—CH_2CH_2—NH—CH_2CH_2—NH—CH_2CH_2—NH_2$, pentaethylenehexamine (PEHA), $H_2N—CH_2CH_2—NH—CH_2CH_2—NH—CH_2CH_2—NH—CH_2CH_2—NH—CH_2CH_2—NH_2$, polyethylene amine, hyperbranched polymers including polyamidoamine dendrimers, polypropylimine dendrimers, polyethyleneimine (PEI), or a mixture thereof.

3. The method of claim 1, wherein the polymeric surface comprises at least one optically transparent polymeric material selected from the group consisting of polyethylene terephthalate (PET, polyethyleneterephthalate), polymethyl methacrylate (PMMA, polymethylmethacylate), polystyrene (PS, polystyrene), and polycarbonate (PC, polycarbonate).

4. The method of claim 1, wherein while applying the gas phase plasma, the liquid composition is contained in a container that is electrically insulating and the container is placed between two electrodes of a plasma chamber.

5. The method of claim 1, wherein the article is in a shape selected from the group consisting of a group consisting of a sheet, a strip, a cavity, a column, a cylinder, a fiber, a coil, a U-shape, a helix and a spiral, wherein the article comprises another surface facing away from the polymer surface, wherein the liquid composition does not contact the other surface and no polymeric layer is formed on the other surface.

6. The method of claim 1, wherein the polymeric surface is referred to as a first polymeric surface, wherein the polymeric layer is referred to as a first polymeric layer, wherein the article comprises a second polymeric surface facing away from the first polymeric surface, wherein the liquid composition also contacts the second polymeric surface and a second polymeric layer is formed on the second polymeric surface as the gas phase plasma is also applied to the liquid composition contacting the second polymeric surface.

7. The method of claim 1, wherein the polymeric surface is referred to as a first surface, wherein the article further comprises a second surface, wherein the first surface contacts the liquid composition while the second surface does not contact the liquid composition while applying the gas phase plasma.

8. The method of claim 7, wherein the article comprises a cavity, wherein the first surface is an inner surface of the cavity, wherein the second surface is facing away from the first surface and located outside the cavity, wherein causing the liquid composition to contact the polymeric surface comprises filling at least part of the cavity with the liquid composition such that the liquid composition contacts the first surface while avoiding contact of the liquid composition onto the second surface.

9. A method of making a nanoparticle layer, the method comprising:

the method of claim 1 to form the polymeric layer on the polymeric surface of the article; and subsequent to forming the polymeric layer, applying metallic nanoparticles onto the polymeric layer to form a single-layer of the metallic nanoparticles over the polymeric layer.

10. The method of claim 9, wherein applying the metallic nanoparticles occurs after completion of applying the gas phase plasma.

11. The method of claim 9, wherein the article is in a shape selected from the group consisting of a group consisting of a sheet, a strip, a cavity, a column, a cylinder, a fiber, a coil, a U-shape, a helix and a spiral, wherein the article comprises another surface facing away from the polymer surface, wherein the liquid composition does not contact the other surface and no polymeric layer is formed on the other surface.

12. The method of claim 9, wherein the polymeric surface is referred to as a first polymeric surface, wherein the polymeric layer is referred to as a first polymeric layer, wherein the article comprises a second polymeric surface facing away from the first polymer surface, wherein the liquid composition also contacts the second polymeric surface and a second polymeric layer is formed on the second polymeric surface as the gas phase plasma is also applied to the liquid composition contacting the second polymeric surface, wherein the metallic nanoparticles are also applied to the second polymeric layer to form a single layer of the metallic nanoparticles over the second polymeric layer.

13. The method of claim 9, wherein the polymeric surface is referred to as a first surface, wherein the article further comprises a second surface, wherein the first surface contacts the liquid composition while the second surface does not contact the liquid composition while applying the gas phase plasma, wherein the single layer of the metallic nanoparticles is formed on the polymeric layer over the first surface while no such layer of metallic nanoparticles is formed over the second surface.

14. The method of claim 13, wherein the article further comprises a film over the second surface such that the liquid composition does not contact the second surface while applying the gas phase plasma.

15. The method of claim 13, wherein the article comprises a cavity, wherein the first surface is an inner surface of the cavity, wherein the second surface is facing away from the first surface and located outside the cavity, wherein causing the liquid composition to contact the polymeric surface comprises filling at least part of the cavity with the liquid composition such that the liquid composition contacts the first surface while avoiding contact of the liquid composition onto the second surface.

16. The method of claim 9, wherein the metallic nanoparticles comprise negatively charged metallic balls, wherein the metallic nanoparticles are bound with free amine terminals of the polymeric layer.

17. The method of claim 9, further comprising one or more ligands attached to the metallic nanoparticles comprising a chemical moiety having specificity to one or more target molecules.

18. The method of claim 9, wherein the metallic nanoparticles have a median size between 1 nm and 10 nm, between 5 nm and 20 nm, between 10 nm and 30 nm, between 20 nm and 40 nm, between 30 nm and 50 nm, between 40 nm and 60 nm, between 50 nm and 80 nm, between 60 nm and 100 nm, between 80 nm and 150 nm, between 100 nm and 200 nm, between 150 nm and 250 nm, between 200 nm and 300 nm, between 250 nm and 400 nm, between 300 nm and 700 nm, or between 500 nm and 900 nm, or between 700 nm and 1100 nm.

* * * * *

UNITED STATES PATENT AND TRADEMARK OFFICE
CERTIFICATE OF CORRECTION

PATENT NO. : 10,060,851 B2
APPLICATION NO. : 14/863238
DATED : August 28, 2018
INVENTOR(S) : Gibum Kim It is certified that error appears in the above-identified patent and that said Letters Patent is hereby corrected as shown below:

In the Specification

In Column 1, Line 61, change "diallydimethylammonium" to --diallyldimethylammonium--

In Column 2, Line 23, change "polymethylmethacylate)," to --polymethylmethacrylate),--

In Column 13, Line 25, change "Capturing," to --Capturing--

In Column 13, Line 29, change "368F." to --368F,--

In Column 16, Line 65, change "660S 1" to --660S1--

In Column 17, Line 27, change "l/e" to --1/e--

In Column 24, Line 37, change "(—PO(OH)$_2$ or —PO(OR)$_2$)" to --(—PO(OH)$_2$ or —PO(OR)$_2$).--

In Column 24, Line 40, change "diallydimethylammonium" to --diallyldimethylammonium--

In Column 25, Line 37, change "polymethylmethacylate)," to --polymethylmethacrylate),--

In Column 26, Line 5, change "polymethylmethacylate)," to --polymethylmethacrylate),--

In Column 30, Lines 8-9, change "tetraoctylamlnonium" to --tetraoctylammonium--

In Column 31, Line 59, change "900," to --90°,--

In the Claims

In Column 35, Lines 31-32, Claim 2, change "diallydimethylammonium" to --diallyldimethylammonium--

Signed and Sealed this
Twelfth Day of March, 2019

Andrei Iancu
*Director of the United States Patent and Trademark Office*

CERTIFICATE OF CORRECTION (continued)
U.S. Pat. No. 10,060,851 B2

In Column 35, Line 51, Claim 3, change "polymethylmethacylate)," to --polymethylmethacrylate),--

In Column 35, Lines 59-60, Claim 5, change "group consisting of a group consisting of a" to --group consisting of a--

In Column 36, Lines 36-37, Claim 11, change "group consisting of a group consisting of a" to --group consisting of a--